United States Patent
George et al.

(10) Patent No.: US 11,413,020 B2
(45) Date of Patent: Aug. 16, 2022

(54) DEEP TISSUE SUPER-RESOLUTION ULTRASOUND IMAGING METHOD AND SYSTEM

(71) Applicant: University of Rochester, Rochester, NY (US)

(72) Inventors: Swetha S. George, Rochester, NY (US); Zeljko Ignjatovic, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 325 days.

(21) Appl. No.: 16/414,229

(22) Filed: May 16, 2019

(65) Prior Publication Data

US 2019/0328366 A1 Oct. 31, 2019

Related U.S. Application Data

(63) Continuation-in-part of application No. PCT/US2017/061501, filed on Nov. 14, 2017.

(60) Provisional application No. 62/425,336, filed on Nov. 22, 2016.

(51) Int. Cl.
*A61B 8/08* (2006.01)
*A61B 8/14* (2006.01)
*A61B 8/00* (2006.01)

(52) U.S. Cl.
CPC .............. *A61B 8/5207* (2013.01); *A61B 8/14* (2013.01); *A61B 8/4488* (2013.01)

(58) Field of Classification Search
CPC ....... A61B 8/5207; A61B 8/14; A61B 8/4488; A61B 5/1077; A61B 8/4494; A61B 8/4483; G06T 11/006; G01S 15/8977
See application file for complete search history.

(56) References Cited

U.S. PATENT DOCUMENTS

| | | | |
|---|---|---|---|
| 6,102,861 A * | 8/2000 | Avila | A61B 8/14 128/916 |
| 7,862,508 B2 * | 1/2011 | Davies | 600/437 |
| 8,818,064 B2 | 8/2014 | Walker et al. | |
| 9,492,139 B2 * | 11/2016 | Rosen | A61B 8/0825 |
| 2007/0083114 A1 | 4/2007 | Yang et al. | |
| 2009/0182237 A1 * | 7/2009 | Angelsen | G01S 15/8918 600/459 |
| 2012/0083695 A1 | 4/2012 | Napolitano et al. | |

(Continued)

FOREIGN PATENT DOCUMENTS

| WO | WO-2010151809 | * 12/2010 | ......... G01S 15/8977 |
|---|---|---|---|
| WO | 2011/163475 | 12/2011 | |
| WO | WO-2013109965 | * 7/2013 | ......... G01S 7/52046 |

OTHER PUBLICATIONS

E. J. Candès and M. B. Wakin, "An introduction to compressive sampling," Signal Processing Magazine, IEEE, vol. 25, No. 2, pp. 21-30, 2008.

(Continued)

*Primary Examiner* — Amanda Lauritzen Moher
*Assistant Examiner* — Nyrobi Celestine
(74) *Attorney, Agent, or Firm* — Ping Wang; Rimon Law

(57) ABSTRACT

Ultrasound imaging at high spatial resolution that makes use of both magnitude and phase of echoes in an image reconstruction process that applies unique constraints to a fitting of echoes from the object of interest to echoes from an array of known scatterers.

27 Claims, 17 Drawing Sheets

(56) References Cited

U.S. PATENT DOCUMENTS

| | | | |
|---|---|---|---|
| 2013/0123635 A1 | 5/2013 | Wegner | |
| 2014/0056104 A1 | 2/2014 | Buechler et al. | |
| 2014/0180112 A1 | 6/2014 | Rothberg et al. | |
| 2014/0180176 A1 | 6/2014 | Rothberg et al. | |
| 2014/0364736 A1* | 12/2014 | Huang | G01S 15/8997 600/447 |
| 2015/0265250 A1* | 9/2015 | Madore | A61B 8/5269 600/440 |
| 2015/0359512 A1* | 12/2015 | Boctor | A61B 8/469 600/444 |
| 2017/0363725 A1 | 12/2017 | Ignjatociv et al. | |

OTHER PUBLICATIONS

E. J. Candes and T. Tao, "Decoding by linear programming," Information Theory, IEEE Transactions on, vol. 51, No. 12, pp. 4203-4215, 2005.

O. Michailovich and D. Adam, "Phase unwrapping for 2-d blind deconvolution of ultrasound images," Medical Imaging, IEEE Transactions on, vol. 23, No. 1, pp. 7-25.

T. Taxt and G. V. Frolova, "Noise robust one-dimensional blind deconvolution of medical ultrasound images," Ultrasonics, Ferroelectrics, and Frequency Control, IEEE Transactions on, vol. 46, No. 2, pp. 291-299, 1999.

J.-F. Synnevåg, A. Austeng, and S. Holm, "Benefits of minimum-variance beamforming in medical ultrasound imaging," Ultrasonics, Ferroelectrics, andFrequency Control, IEEE Transactions on, vol. 56, No. 9, pp. 1868-1879, 2009.

S. Holm, J. Synnevag, and A. Austeng, "Capon beamforming for active ultrasound imaging systems," in Proc. IEEE, 13th DSP Workshop, 2009.

J. A. Mann and W. Walker, "A constrained adaptive beamformer for medical ultrasound: Initial results," in Ultrasonics Symposium, 2002. Proceedings. 2002 IEEE, vol. 2. IEEE, 2002, pp. 1807-1810.

I. K. Holfort, F..Gran, and J. A. Jensen, "Minimum variance beamforming for high frame-rate ultrasound imaging," in Ultrasonics Symposium,2007. IEEE. IEEE, 2007, pp. 1541-1544.

B. M. Asl and A. Mahloojifar, "Eigenspace-based minimum variance beamforming applied to medical ultrasound imaging," Ultrasonics, Ferroelectrics, and Frequency Control, IEEE Transactions on, vol. 57, No. 11, pp. 2381-2390, 2010.

C. Quinsac, A. Basarab, J. Gregoire, and D. Kouame, "3d compressed sensing ultrasound imaging," in Proc. IEEE Int. Ultrason. Symp.(IUS), San Diego,USA, 2010.

C. Quinsac, A. Basarab, J.-M. Girault, and D. Kouamé, "Compressed sensing of ultrasound images: sampling of spatial and frequency domains," in Signal Processing Systems (SIPS), 2010 IEEE Workshop on. IEEE, 2010, pp. 231-236.

M. Schiffner, T. Jansen, and G. Schmitz, "Compressed sensing for fast image acquisition in pulse-echo ultrasound," Biomedical Engineering/Biomedizinische Technik, vol. 57, No. SI-1 Track-B, pp. 192-195, 2012.

N. Wagner, Y. C. Eldar, A. Feuer, G. Danin, and Z. Friedman, "Xampling in ultrasound imaging," CoRR, vol. abs/1104.5327, 2011.

N. Wagner, Y. C. Eldar, A. Feuer, and Z. Friedman, "Compressed beamforming applied to b-mode ultrasound imaging," in Biomedical Imaging (ISBI), 2012 9th IEEE International Symposium on. IEEE, 2012, pp. 1080-1083.

D. Friboulet, H. Liebgott, and R. Prost, "Compressive sensing for raw rf signals reconstruction in ultrasound," in Ultrasonics Symposium (IUS), 2010 IEEE. IEEE, 2010, pp. 367-370.

H. Liebgott, R. Prost, and D. Friboulet, "Pre-beamformed rf signal reconstruction in medical ultrasound using compressive sensing," Ultrasonics, vol. 53, No. 2, pp. 525-533, 2013.

P. Blomgren, G. Papanicolaou, and H. Zhao, "Super-resolution in time-reversal acoustics," The Journal of the Acoustical Society of America, vol. 111, No. 1, pp. 230-248, 2002.

A. J. Devaney, "Super-resolution processing of multi-static data using time reversal and music," 2000.

Y. Labyed and L. Huang, "Super-resolution ultrasound imaging using a phase-coherent music method with compensation for the phase response of transducer elements," Ultrasonics, Ferroelectrics, and Frequency Control, IEEE Transactions on, vol. 60, No. 6, pp. 1048-1060, 2013.

M. A. O'Reilly and K. Hynynen, "A super-resolution ultrasound method for brain vascular mapping," Medical physics, vol. 40, No. 11, p. 110701, 2013.

B. Cox and P. Beard, "Imaging techniques: Super-resolution ultrasound," Nature, vol. 527, No. 7579, pp. 451-452, 2015.

C. Errico, J. Pierre, S. Pezet, Y. Desailly, Z. Lenkei, O. Couture, and M. Tanter, "Ultrafast ultrasound localization microscopy for deep super-resolution vascular imaging," Nature, vol. 527, No. 7579, pp. 499-502, 2015.

T. Dertinger, R. Colyer, R. Vogel, J. Enderlein, and S. Weiss, "Achieving increased resolution and more pixels with superresolution optical fluctuation imaging (soft)," Optics express, vol. 18, No. 18, pp. 18 875-18 885, 2010.

T. Taxt and R. Jirik, "Superresolution of ultrasound images using the first and second harmonic signal," Ultrasonics, Ferroelectrics, and Frequency Control, IEEE Transactions on, vol. 51, No. 2, pp. 163-175, 2004.

D. Kouame and M. Ploquin, "Super-resolution in medical imaging: An illustrative approach through ultrasound," in Biomedical Imaging: From Nano to Macro, 2009. ISBI'09. IEEE International Symposium on. IEEE, 2009, pp. 249-252.

G. Clement, J. Huttunen, and K. Hynynen, "Superresolution ultrasound imaging using back-projected reconstruction," The Journal of the Acoustical Society of America, vol. 118, No. 6, pp. 3953-3960, 2005.

J. N. Wright, "Image formation in diagnostic ultrasound," 1997.

J. W. Goodman, "Introduction to fourier optics," 2005.

T. Szabo, Diagnostic Ultrasound Imaging: Inside Out, ser. Academic Press series in biomedical engineering. Elsevier Academic Press, 2004. [Online]. Available: https://books.google.com/books?id=-Fd1Pkeh2T0C.

B. R. Hunt, "Super-resolution of imagery: understanding the basis for recovery of spatial frequencies beyond the diffraction limit," in Information, Decision and Control, 1999. IDC 99. Proceedings. 1999. IEEE, 1999, pp. 243-248.

E. J. Candès and C. Fernandez-Granda, "Towards a mathematical theory of super-resolution," CoRR, vol. abs/1203.5871, 2012.

B. E. Treeby, J. Jaros, A. P. Rendell, and B. Cox, "Modeling nonlinear ultrasound propagation in heterogeneous media with power law absorption using a k-space pseudospectral method," The Journal of the Acoustical Society of America, vol. 131, No. 6, pp. 4324-4336, 2012.

Swetha George et al: A novel ultrasound imaging technique for portable and high speed imaging[1] IEEE 13th International New Circuits and System Conference (NEWCAS). Jun. 7, 2015, pp. 1-4.

Apr. 19, 2016 International Search Report and Written Opinion in connection with International Application No. PCT/US2015/065722.

Mar. 5, 2018 International Search Report and Written Opinion in connection with International Application No. PCT/US2017/061501.

Charles J. Pavlin et al. "Advances in Ultrasound Biomicroscopy," Ultrasound in Medicine & Biology, vol. 26, No. 1, pp. 1-27, Feb. 2000.

Viola et al. "Time-Domain Optimized Near-Field Estimator for Ultrasound Imaging: Initial Development and Results", NIH Public Acess Author Manuscript, Jan. 2008.

Ellis et al., Super-Resolution Image Reconstruction With Reduced Computational Complexity, 2009 IEEE Ultrasonics Symposium Proceedings, p. 2351-2354.

Ellis et al., Super-Resolution Image Reconstruction Using Diffuse Source Models, NIH Public Access Author Manuscript, Jun. 2010.

Yankelevsky et al., Component Based Modeling Of Ultrasound Signals, Mar. 1, 2016.

AAPM/RSNA Physics Tutorial for Residents: Topics in US B-mode US: Basic Concepts and New Technology.

(56) References Cited

OTHER PUBLICATIONS

R. Kazys, L. Svilainis, and L. Mazeika, "Application of orthogonal ultrasonic signals and binaural processing for imaging of the environment," Ultrasonics, vol. 38, No. 1-8, pp. 171-175, Mar. 2000.
Parker, Kevin J., "Superresolution imaging of scatterers in ultrasound B-scan imaging," The Journal of the Acoustical Society of America, 131, 4680-4689 (2012).
Jensen, J. A., "Deconvolution of ultrasound images," Ultrasonic Imaging, vol. 14, Issue 1, pp. 1-15, 1992.
Alam, S. K., Ophir, J., Cespedes, I., and Varghese T. "A deconvolution filter for improvement of time-delay estimation in elastography," IEEE Trans. Ultrason. Ferroelectr. Freq. Control 45, pp. 1565-1572 (1998).
Michailovich, O., and Adam, D., "Phase unwrapping for 2-D blind deconvolution of ultrasound images," IEEE Trans. Med. Imaging 23, pp. 7-25, 2004.
Shin, H. C., Prager, R., Gomersall, H., Kingsbury, N., Treece, G., and Gee, A., "Estimation of average speed of sound using deconvolution of medical ultrasound data," Ultrasound Med. Biol. 36, pp. 623-636, 2010.
Synnevag, J.-F.; Austeng, A.; Holm, S., "Minimum variance adaptive beamforming applied to medical ultrasound imaging," Ultrasonics Symposium, 2005 IEEE, vol. 2, No., pp. 1199,1202, Sep. 18-21, 2005.
Asl, B.M.; Mahloojifar, A., "Minimum variance beamforming combined with adaptive coherence weighting applied to medical ultrasound imaging," Ultrasonics, Ferroelectrics, and Frequency Control, IEEE Transactions on, vol. 56, No. 9, pp. 1923-1931, Sep. 2009.
Asl, B.M.; Mahloojifar, A., "Eigenspace-based minimum variance beamforming applied to medical ultrasound imaging," Ultrasonics, Ferroelectrics, and Frequency Control, IEEE Transactions on, vol. 57, No. 11, pp. 2381,2390, Nov. 2010.
T. Chernyakova and Y. C. Eldar, "Fourier Domain Beamforming: The Path to Compressed Ultrasound Imaging", IEEE Transactions on Ultrasonics, Ferroelectronics, and Frequency Control, vol. 61, issue 8, pp. 1252-1267, Jul. 2014.
N. Wagner, Y. C. Eldar and Z. Friedman, "Compressed Beamforming in Ultrasound Imaging", IEEE Transactions on Signal Processing, vol. 60, issue 9, pp. 4643-4657, Sep. 2012.
R. Tur, Y. C. Eldar, and Z. Friedman, "Innovation rate sampling of pulse streams with application to ultrasound imaging," IEEE transactions on Signal Processing, 2011.
S. Campbell, A Short History of Sonography in Obstetrics and Gybnecology, : Facts Views Vis Obgyn 2013, v.5(3): pp. 213-229.
F.J. Fry, J. E. Barger, "Acoustical properties of the human skull," J. Acoust. Soc. Am. 63, 1576 (1978).
P.J. White, G.T. Clement, K. Hynynen, Longitudinal and shear mode ultrasound propagation in human skull bone, Ultrasound in Medicine & Biology, vol. 32, Issue 7, Jul. 2006, pp. 1085-1096.
N. Petridou, M. Italiaander, B. L. van de Bank, J. C. W. Siero, P. R. Luijten and D. W. J. Klomp, "Pushing the limits of high-resolution functional MRI using a simple high-density multi-element coil design," NMR in Biomedicine, ISSN 0952-3480, Jan. 2013, vol. 26, Issue 1, pp. 65-73.
Schmutzhard, S.; Jung, A.; Hlawatsch, F., "Minimum variance estimation for the sparse signal in noise model," Information Theory Proceedings (ISIT), 2011 IEEE International Symposium on, vol., No., pp. 124,128, Jul. 31, 2011-Aug. 5, 2011.
Juhwan Yoo; Becker, S.; Monge, M.; Loh, M.; Candes, E.; Emami-Neyestanak, A., "Design and implementation of a fully integrated compressed-sensing signal acquisition system," Acoustics, Speech and Signal Processing (ICASSP), 2012 IEEE International Conference on, vol., No., pp. 5325,5328, Mar. 25-30, 2012.

J.W. Goodman, Statistical Optics., Wiley-Interscience, New York, 1985.
Burckhardt, C.B., "Speckle in ultrasound B-mode scans," Sonics and Ultrasonics, IEEE Transactions on, vol. 25, No. 1, pp. 1,6, Jan. 1978.
Ouyang, G. "Laser speckle reduction based on angular diversity induced by Piezoelectric Benders," Journal of the European Optical Society—Rapid Publications, ISSN 1990-2573, 2013, vol. 8, p. 4.
M. N. Akram, Z. Tong, G. Ouyang, X. Chen, and V. Kartashov, "Laser speckle reduction due to spatial and angular diversity introduced by fast scanning micromirror," Appl. Optics 49(17), 3297-3304 (2010).
J. A. Jensen, "FIELD: a program for simulating ultrasound systems," in 10th Nordicbaltic Conference on Biomedical Imaging, Supplement 1, Part 1, vol. 34, 1996, pp. 351-353.
T. Hastie, R. Tibshirani, and J. Friedman, The Elements of Statistical Learning, 2nd ed. New York: Springer, 2009.
R. Tibshirani, "Regression shrinkage and selection via the lasso," J. Roy. Stat. Soc. B, vol. 58, pp. 267-288, 1996.
M. W. Mahoney, "Randomized algorithms for matrices and data," Foundations and Trends in Machine Learn., vol. 3, No. 2, pp. 123-224, 2011.
K. L. Clarkson and D. P. Woodruff, "Low rank approximation and regression in input sparsity time," in Proc. Symp. Theory Computing, Jun. 1-4, 2013, pp. 81-90.
K. Slavakis, G. B. Giannakis, and G. Mateos, "Modeling and optimization for Big Data analytics," IEEE Signal Processing Magazine, vol. 31, No. 5, pp. 18-31, Sep. 2014.
V. M. Patel, H. V. Nguyen, and R. Vidal, "Latent space sparse subspace clustering," in Proc. of Intl. Conf. Computer Vision, Sydney: Australia, 2013.
S. Shalev-Shwartz, "Online learning and online convex optimization," Foundations and Trends in Machine Learning, vol. 4, No. 2, pp. 107-194, 2012.
M. Mardani, G. Mateos, and G. B. Giannakis, "Dynamic anomalography: Tracking network anomalies via sparsity and low rank," IEEE Journal of Sel. Topics in Signal Processing, vol. 8, Feb. 2013.
M. Mardani, G. Mateos, and G. B. Giannakis, "Decentralized sparsity-regularized rank minimization: Algorithms and applications," IEEE Trans. on Signal Processing, vol. 61, pp. 5374-5388, Nov. 2013.
G. Mateos, J. A. Bazerque, and G. B. Giannakis, "Distributed sparse linear regression," IEEE Trans. Signal Processing, vol. 58, No. 10, pp. 5262-5276, Oct. 2010.
G. Mateos, I. D. Schizas, and G. B. Giannakis, "Distributed recursive least-squares for consensus- based in-network adaptive estimation," IEEE Transactions on Signal Processing, vol. 57, No. 11, Nov. 2009.
K. Slavakis, S.-J. Kim, G. Mateos, and G. B. Giannakis, "Stochastic approximation vis-a-vis online learning for Big Data," IEEE Signal Processing Magazine, vol. 31, No. 6, pp. 124-129, Nov. 2014.
F. Bensaali, A. Amira, R. Sotudeh, "Floating-point matrix product on FPGA", Proc. IEEE/ACS Int. Conf. on Computer Systems and Applications, pp. 466-473, 2007.
C.Y. Lin, H.K.-H. So, P.H. Leong, "A model for matrix multiplication performance on FPGAs", Proc. International Conference on Field Programmable Logic and Applications, pp. 305-310, Sep. 2011.
J. Fowers, K. Ovtcharov, "A High Memory Bandwidth FPGA Accelerator for Sparse Matrix-Vector Multiplication", Proc. IEEE 22nd International Symposium on Field-Programmable Custom Computing Machines. pp. 36-43, May 2014.
Z. Jovanovic, V. Milutinovic, "FPGA accelerator for floating-point matrix multiplication", IET Computers & Digital Techniques, 6(4): 249-256.

* cited by examiner

DEEP TISSUE SUPER-RESOLUTION ULTRASOUND IMAGING METHOD AND SYSTEM

CROSS-REFERENCE TO PRIOR APPLICATIONS

This application is a continuation, with added subject matter, of International Application PCT/US17/61501 filed Nov. 14, 2017 and claiming priority to U.S. Provisional Application Ser. No. 62/425,336 filed on Nov. 22, 2016. The application claims priority to and incorporates by reference the entire contents of said International and Provisional applications.

FIELD

This patent application pertains to ultrasound imaging of objects, especially in medical imaging, and more specifically relates to imaging at high spatial resolution that makes use of both magnitude and phase of echoes in an image reconstruction process that applies unique constraints to a fitting of echoes from the object of interest to echoes from an array of known scatterers.

BACKGROUND

Super-resolution imaging or sub-wavelength imaging has become a popular domain of research particularly in medical imaging. Over the past couple of decades, the world of imaging has seen drastic improvement in the resolution as well as image quality with the help of improved hardware and efficient image processing algorithms. Ultrasound can be a preferred medical imaging modality due to its non-ionizing, non-invasive and relatively inexpensive nature. A desire to achieve high resolution in ultrasound imaging comparable to that of MRIs, CTs and X-ray tomography, has fueled extensive research aimed at improving resolution and speed of acquisition of ultrasound images. High frequency ultrasonic imaging systems often termed ultrasonic biomicroscope or UBM have become popular for imaging shallow tissue structures such as the skin and eyes as well as small animals. The UBM systems work at frequencies between 30-60 MHz and sometimes higher.

Over the past few years, compressive sensing [1] [2], deconvolution [3] [4] and adaptive/minimum-variance beamforming [5-9] have been researched and applied to the field of medical imaging. Compressive sensing, which is based on assuming sparsity at certain steps during the imaging process, has helped reduce the amount of data accrued and/or used for image reconstruction. It can be done in a few ways: a) By assuming a sparse scatterer distribution or b) assuming sparsity in the beamformed RF image or c) utilizing sparse RF data at the receiver [10-11]. The sparse scatterer map based compressive sensing methods discussed in [12] integrate single plane wave transmission for high frame rate imaging while achieving resolution comparable to that of conventional ultrasound. Another technique called Xampling [13-14], has imaged macroscopic perturbations from real cardiac ultrasound data with reduced speckle content. The authors in [15] and [16] discuss image reconstruction from sub-sampled raw RF data and present results that have comparable resolution to conventional ultrasound while using less than 30% of the original RF samples acquired before beamforming. Adaptive beamforming techniques have demonstrated improvement in image resolution with the help of reduced main lobe width and low side lobe levels. Adaptive beamformers calculate the weights for receive apodization based on the recorded data rather than using pre-calculated values. The authors in [5] and [6] report better resolution compared to delay-and-sum beamformers while using a smaller aperture and parallel receive beamforming by a minimum variance beamformer method. These and other techniques aim to achieve resolution equivalent to conventional ultrasound while reducing the RF data required for reconstruction. Super-resolution (SR) or submillimeter imaging, on the other hand, aims at reducing the dependence of resolution on pulse shape and width as well as the presence of speckles to achieve higher resolution.

There are super-resolution techniques that obtain images by combining many low resolution images and applying post image processing techniques. Super-resolution through time reversal acoustics can also be achieved due to the random nature of inhomogeneous media. Authors of [17] and [18] report results that indicate sub-wavelength imaging through time reversal acoustics. The phase-coherent multiple signal classification (MUSIC) method discussed in [19] is said to improve ultrasound resolution to a quarter of a wavelength. This method assumes a grid size smaller than the transducer length and the results are presented for frequencies in the 4-11 MHz range and at a depth of a couple centimeters. Several research groups [20-22] have used gas micro-bubbles for submillimeter ultrasound imaging in vascular systems that are in the near-field of imaging (few millimeters) and report tenfold improvement in resolution compared to conventional ultrasound. Another research group [23] reports improving the temporal resolution and acquisition times seen in ultrasound localized microscopy by applying a super-resolution optical fluctuation imaging method. Research presented in [24] discusses a blind 2-D deconvolution technique based on an improved phase-unwrapping technique applied to the pulse estimation and reports images with sharper tissue boundaries when compared to the images before deconvolution. Another group of authors [25] describes a methodology that consists of performing parametric modeling on the Fourier transform of the Hilbert transform of the RF data and achieves sub-wavelength resolution at higher frequencies (20 MHz in their results). Clement et. al [26] describe a super-resolution image recovery technique based on Fourier spatial frequency spectrum analysis of the signals that are backprojected in the wave-vector domain to the focal plane. Their technique is used to estimate the size and location of the object and were able to detect a human hair with diameter $0.09\lambda$ at 4.7 MHz at a few tens of millimeters depth.

Additional techniques for supper-resolution and related processing are discussed in [33]-[38], and some are understood to involve using modeling in which initial echoes from a model are processed with echoes from an actual object to ultimately generate an image of a region of interest in the object.

Most of the techniques referred to above aim for high resolution for superficial tissue imaging/characterization rather than deep tissue imaging at depths of a few hundred wavelengths.

SUMMARY

An object of the new approach described in this patent specification is super-resolution ultrasound imaging that involves the pre- and post-processing that estimates ultrasound images of an actual object from information derived from a priori knowledge of a sensing matrix. The desired images can be formed from the echoes (RF data) after only a single plane wave excitation of the object with the help of a least squares with novel constraints. The process can be extended to 3D.

One embodiment comprises an ultrasound transducer that sends ultrasound into an object from plural sending transducer elements and receives echoes from the object at fewer but no less than two elements of the transducer, without apodization or beam forming. A computer memory stores a sensing matrix of reflectance coefficients that when applied to an array of known scatterers produces echoes that said fewer receiving elements of the transducer receive or would have received from the scatterers in response to ultrasound that is the same as or approximates the ultrasound the transducer sends into the object. A computer processor estimates ultrasound properties of locations in the object that spatially relate to said array of scatterers by applying a bounded least squares estimation process to fit the echoes received from the object to a combination of the sensing matrix and properties of said location in the object. The estimation process constrains the properties of the locations in the object to positive values between zero and one. The computer then produces and displays an ultrasound image of the object as a function of said estimated ultrasound properties.

Another embodiment is an ultrasound imaging system comprising an ultrasound transducer having an array of transducer elements configured to detect both amplitude and phase of echoes from an object at fewer but not less than two of the transducer elements from which the transducer has sent ultrasound into be object to cause said echoes, a computer memory storing reflectance coefficients that when applied to an array of known scattering locations results in echoes that were or would have detected at said fewer transducer elements caused by ultrasound the transducer is configured to send into the object, and a computer processor configured to estimate ultrasound properties of locations in the object that spatially relate to said array of scatterers by applying a bounded least squares estimation process to fit the echoes received from the object to a combination of the sensing matrix and properties of said location in the object. The estimation process is configured to constrain the properties of said locations in the object to positive values between a minimum and a maximum. The computer processor is further configured to produce and display an ultrasound image of the object as a function of said estimated ultrasound properties. The constrained values can range from zero to one.

This patent specification further describes an ultrasound imaging method comprising sending ultrasound into an object from plural transducer elements and receiving echoes from the object at fewer but no less than two of the transducer elements, without apodization or beam forming, providing a sensing matrix that when applied to an array of known scatterers produces echoes that said fewer transducer elements receive or would have received from the scatterers in response to ultrasound approximating the ultrasound sent into the object, carrying out a bounded estimation process with a computer to fit the echoes received from the object to a combination of the sensing matrix and properties of locations in the object spatially related to said scatterers, wherein said estimation process is configured to constrain the properties of said locations in the object to positive values between zero and one, and producing and displaying an ultrasound image of the object as a computer-calculated function of said estimated ultrasound properties.

In another embodiment, an ultrasound imaging process comprises detecting both amplitude and phase of echoes from an object at fewer but not less than two of plural transducer elements from which ultrasound has been sent into the object to cause said echoes, providing a sensing matrix that when applied to an array of known scatterers produces echoes that said fewer transducer elements receive or would have received from the scatterers in response to ultrasound approximating the ultrasound sent into the object, carrying out an estimation process with a computer programmed to fit the echoes received from the object to a combination of the sensing matrix and properties of location in the object spatially related to said scatterers through a bounded least squares process, wherein said estimation process is configured to constrain the properties of said locations in the object to positive values between a minimum and a maximum, and producing and displaying an ultrasound image of the object as a computer-calculated function of said estimated ultrasound properties. The positive values can range from zero to one.

BRIEF DESCRIPTION OF THE DRAWINGS

FIG. 11*b* shows an image of the same object produced with the new approach described in this patent specification.

DETAILED DESCRIPTION

A detailed description of examples of preferred embodiments is provided below. While several embodiments are described, the new subject matter described in this patent specification is not limited to any one embodiment or combination of embodiments described herein, but instead encompasses numerous alternatives, modifications, and equivalents. In addition, while numerous specific details are set forth in the following description to provide a thorough understanding, some embodiments can be practiced without some of these details and even without all of the described details. Moreover, for clarity and conciseness, certain technical material that is known in the related technology have not been fully described in detail, to avoid unnecessarily obscuring the new subject matter described herein. It should be clear that individual features of one or several of the specific embodiments described herein can be used in combination with features of other described embodiments or with other features. Further, like reference numbers and designations in the various drawings indicate like elements.

Figure 1:
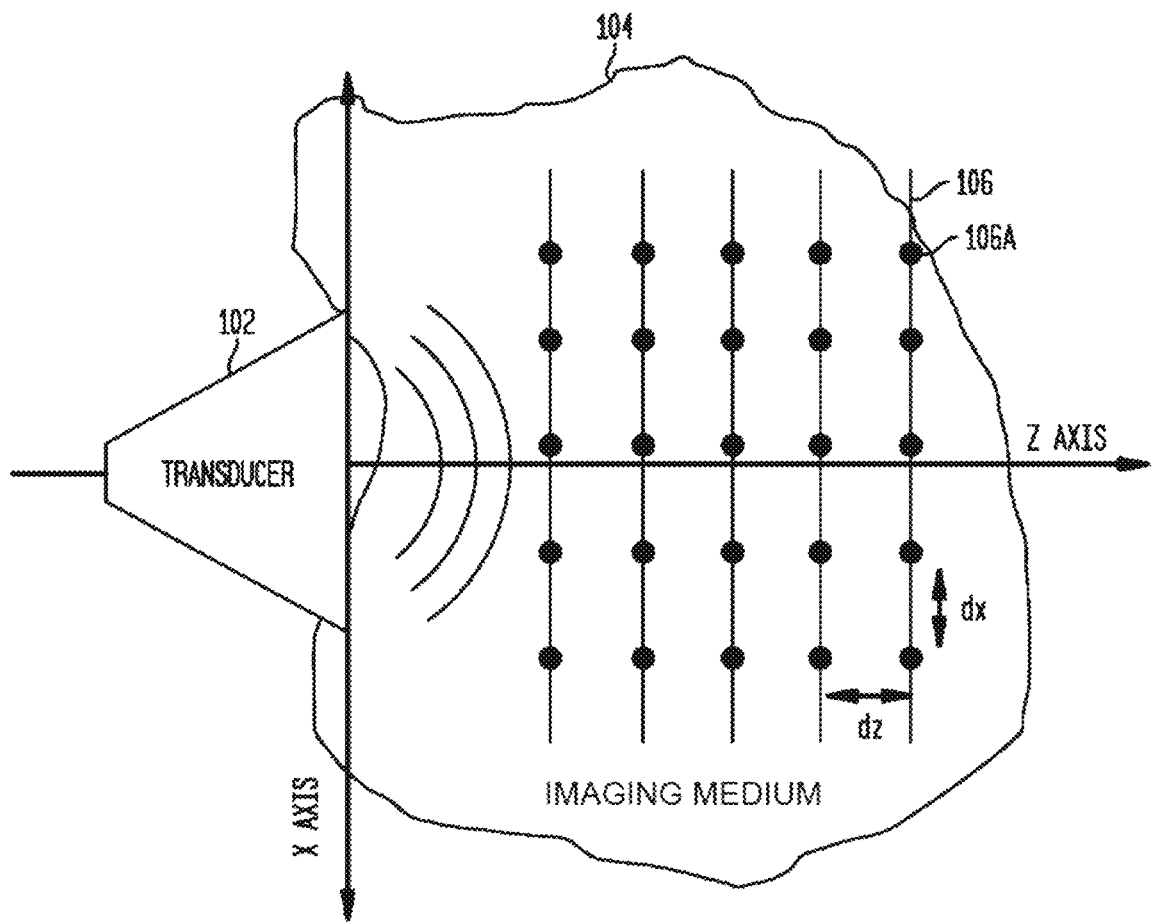
FIG. 1 illustrates an object, an ultrasound transducer, and an array of scaterrers superimposed on a region of interest on the object to provide a sensing matrix used in estimating an ultrasound image of a region of interest in the object.

Referring to FIG. 1, an ultrasound transducer 102 has plural transducer elements such as 48 elements and is acoustically coupled with an object or body 104 and configured to send transmitted ultrasound such as a plane wave into object 104 from all the transducer elements, without apodization of beam forming. Transducer 102 detects echoes from object 104 at fewer but not less than 2 of its elements, for example at the two end elements in the case of a linear array of 48 elements. The transducer can have a different, typically greater, number of transducer elements, and can detect echoes at more than two of the elements so long as the detecting elements are fewer, and typically much fewer, than the elements that transmit ultrasound into object 104. And, the transducer elements can be arranged other than in a linear array, for example in plural linear arrays, in one or more curved arrays, or in a 2D pattern that can be periodic or non-periodic. Also illustrated in FIG. 1 is a grid 106 defining an array of scatterers or scattering points 106*a* spaced from each other in one direction by distances dx and by distances dz in another direction. Distances dx and dz can be the same or different. Grid 106 can be square as illustrated, or rectangular, or in some other shape, and can be periodic as illustrated or non-periodic, and can be defined in a coordinate system other than an x-z system, such as in polar coordinates. Grid 106 is a notional rather than an actual grid and, as described below, is used in estimating an ultrasound image representing locations in object 104 that spatially match locations of scatterers 106*a* when grid 106 is notionally superimposed on a region of interest in object 104.

In principle, the new approach described in this patent specification derives or provides a sensing matrix that, when applied to a known array of scatterers, results in echoes that those scatterers produce or would have produced in response to ultrasound that approximates the ultrasound that transducer 102 sends into object 104. A process with unique bounding fits the echoes received from the object to a combination such a product of the sensing matrix and ultrasound properties of locations in the object that spatially relate to said scatterers, and produces an ultrasound image of a region of interest that comprises said locations in the object. The process can include bounded least squares operation that constrains the properties being estimated to a range of positive values such as zero to one. An image of a region of interest in the object is produced as a function of the estimated ultrasound properties.

First, a theoretical basis is laid out below, followed by implementation examples.

A few essential equations are described below. A fluid model is assumed for propagation of ultrasound waves, so the waves that travel in a medium used in this discussion are longitudinal in nature and have an associated wavenumber $k=\omega/c$, where $\omega=2\pi \tilde{f}$ and $\tilde{f}$ is the spatial frequency. Particle velocity in the medium is given by $$v = \frac{\partial u}{\partial t},$$

where u is the particle displacement. For convenience, the particle velocity is also expressed as the gradient of velocity potential, $\nabla \phi$. The pressure is then given by $$p = -\rho \frac{\partial \phi}{\partial t}.$$

The plane wave equation (three dimensional) that governs acoustic propagation in an ideal medium is given by [27]:

$$\nabla^2 \phi(x, y, z, t) - \frac{1}{c^2} \frac{\partial^2}{\partial t^2} \phi(x, y, z, t) = 0 \quad (1)$$

where c is the propagation velocity in the medium. $\phi(x, y, z, t)$ is the pressure or the velocity potential at the location (x, y, z). The Helmholtz wave equation in (1) is in general assumed to be linear and time shift invariant in both time and space. In the frequency domain, Eq. (1) can be expressed as, $$\nabla^2 \varphi + k^2 \varphi = 0 \quad (2)$$

where $\varphi$ is the Fourier transform of $\phi$. k is the wavevector and can be broken down into its projections in the x, y, and z directions as $k^2 = k_x^2 + k_y^2 + k_z^2$. Analogous to the time domain waveform having a spectrum consisting of a collection of frequencies, the acoustic field of a transducer has an angular spectrum of plane waves [28]. As such, a Fourier transform relation can be established between the amplitude of the source and the spatial frequency distribution as discussed in Szabo [29].

The finer details of an object are often recovered from the higher spatial frequencies. In a way, the imaging system acts as a filter where the resulting signal is a convolution of the object, g, with the point spread function of acoustic system, say h. A mathematical model describing the imaging process is shown in Eq. (3).

$$y=h(x)*g(x) \quad (3)$$

In the frequency domain, this equation becomes, $$Y=H(\tilde{f})G(\tilde{f}) \quad (4)$$

where H is called the modulation transfer function (MTF), G is the Fourier transform of g and Y is Fourier transform of y. Due to the finite aperture size of the transducer, there is a low-pass cutoff frequency above which information is typically lost. Typically, the MTF has spectral notches (or zeros) rendering the convolution operation in Eq. (3) non-invertible. Consequently, only the spectral components below the first spectral notch (i.e., spatial frequency components below the diffraction limit) can be uniquely recovered. During the measurement process in most imaging systems, only coarse features of the object g are obtained, thus not being able to resolve the finer details. Per results presented in [30] by Hunt, when a wave is reflected by a scatterer, it introduces high frequency spatial content which affects the spatial frequencies below the cutoff spatial frequency ω/c. As such the problem of super-resolution is one that involves recovering the fine details of an object being imaged with the coarse measurements from the spectrum below the cut-off spatial frequency.

Work reported in [30-31] informs that super-resolution can be achieved if certain conditions like positivity, compactness, or sparsity are assumed for the support of the signal g during the process of image reconstruction. In some cases, this has been achieved with the help of a priori information [12], [26], and [31]. This can be recognized as a starting point for the sub-wavelength ultrasound imaging technique described in this patent specification.

A discussion follows of main steps of an example of image reconstruction per principles described in this patent specification.

The analysis of ultrasound systems [29] begins with the pulse-echo equation of the echo, r(t), as given in Eq. (5).

$$r(t) = k \frac{e^{\mu_a t}}{(ct)^2} \int_0^\infty \int_{-\infty}^\infty \int_{-\infty}^\infty R(x, y, z) n(t - 2c^{-1}z) \tilde{q}^2(x, y, z) dx dy dz \quad (5)$$

where $\tilde{q}^2(x,y,z)=z\tilde{q}(x,y,z)$. $\tilde{q}(x,y,z)$ is the transducer field pattern, c is the speed of sound in the medium, and k is the wavenumber. $\mu_a$ accounts for the attenuation in the medium being imaged. R(x,y,z) is the scatterer strength or reflectivity. In traditional B-mode ultrasound, only the magnitude of the received signal R(x,y,z) is used during image reconstruction to form each A-line. But in the super resolution ultrasound system described in this patent specification, both the phase and amplitude are used for the image reconstruction process. In the technique example described below, a plane wave is sent out from a linear transducer array and the received echoes are stored without applying apodization or beamforming and thus being able to conserve the phase information.

Consider the case of two-dimensional imaging in the x-z plane where the axis of propagation is in the z direction (refer to FIG. 1). A transducer 102 sends a plane wave ultrasound into an object 104 (a medium such as tissue). A two-dimensional grid 106 of scatterers 106a is formulated to overlay the object with $N_X$ and $N_Z$ as the dimensions in the x and z directions, respectively. We then define a reflectivity matrix $R_{N_X \times N_Z}^g$, where each element $r_{ij}$ corresponds to a reflectivity of a point scatterer 106a in the object at every grid point $x_i$ and $z_j$. A column vector $X_{N_X N_Z \times 1}$ is then formed by concatenating the columns of the matrix $R^g$ as shown below, where $R_j^g$ is the $j^{th}$ column of the matrix.

$$X_{N_X N_Z \times 1} = \begin{bmatrix} R_1^g \\ R_2^g \\ \cdot \\ \cdot \\ R_N^g \end{bmatrix}$$

Now we form a sensing or imaging matrix A. The matrix A can be described as a set of column vectors that correspond to the spatial impulse response (or signal received by the transducer array, which can be called echoes detected or received by transducer 102) when only one point scatterer 106a with maximum reflectivity is present in the object as shown in Eq. (6). Let us assume that the array has $N_C$ receive channels and each channel takes a total of $N_S$ samples per frame per acquisition. The imaging matrix A is then of the size $N_C N_S$ by $N_x N_z$. For example, a column vector $\tilde{A}_{N_C N_S \times 1}^1$ corresponds to the signal samples (echoes) received by the transducer array 102 from a point scatterer 106a located at (1,1) on the grid of size ($N_X$, $N_Z$).

Figure 2:
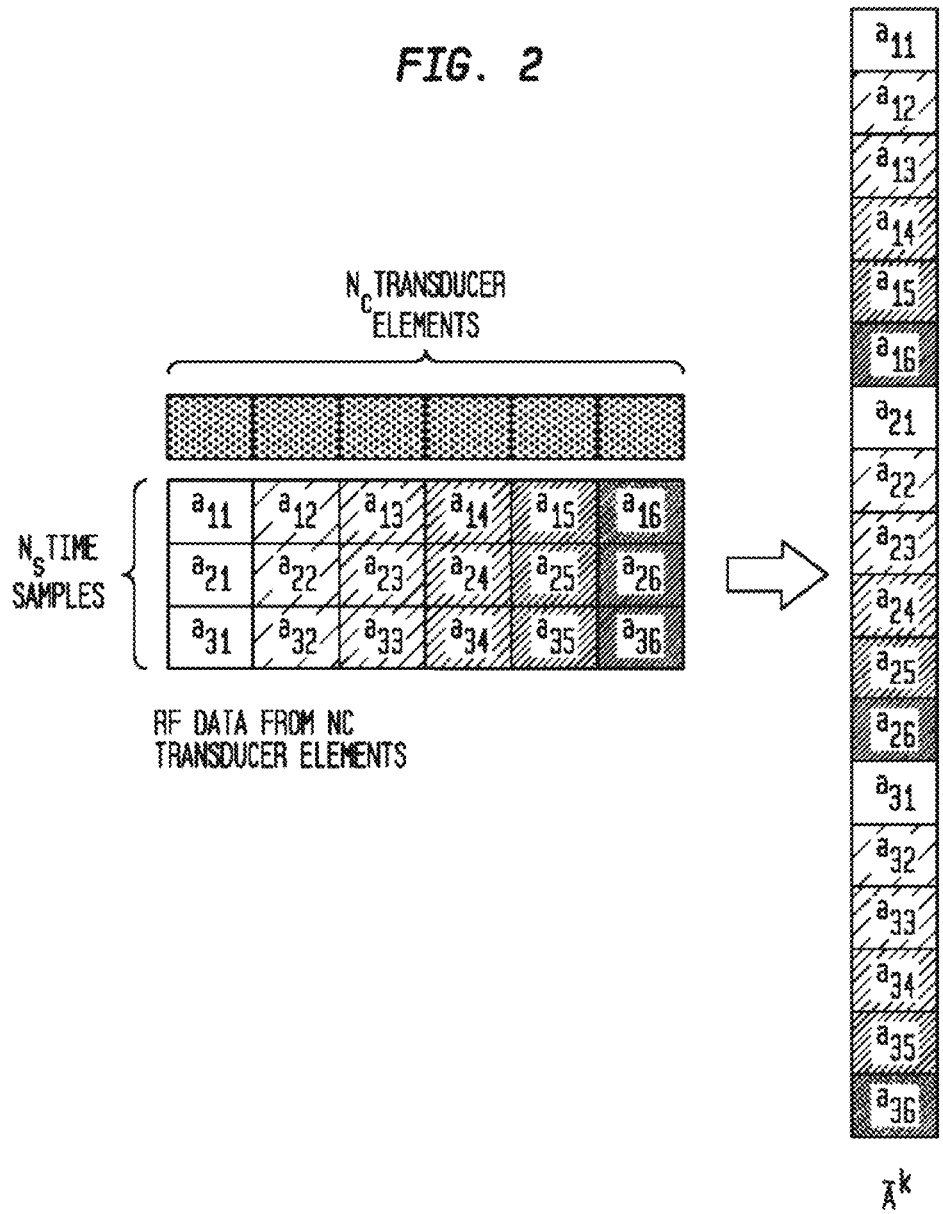
FIG. 2 illustrates an example of creating a sensing or imaging matrix.

FIG. 2 illustrates the formation of one column vector of sensing or imaging matrix A. Since matrix A is calculated prior to the process of imaging an object 104, it can be considered a priori information. The sensing or imaging matrix can be written as below, $$A=[\tilde{A}^1 \tilde{A}^2 \ldots \tilde{A}^{N_x N_z}]_{N_C N_S \times N_x N_z} \quad (6)$$

The received RF data (echoes) from grid points of any target phantom will be a linear combination of the vectors in the imaging matrix A. From here the imaging model can be formulated as shown below, $$Y_{N_C N_S \times 1} = A_{N_C N_S \times N_x N_z} X_{N_x N_z \times 1} + E_{N_C N_S \times 1} \quad (7)$$

where E is a column vector of samples of white Gaussian noise process with covariance matrix $C_E$, Y is the measured raw RF data, and X is a column vector of reflectance coefficients to be estimated. Estimation in the ultrasound imaging method in this example is carried out using the least squares estimation algorithm, which finds an estimate of the column vector $\hat{X}_{N_x N_z \times 1}$ that minimizes L2-norm of the error term ε=AX−Y as shown in Eq. (8).

$$\hat{X}_{N_x N_z \times 1} = \underset{X}{\operatorname{argmin}}(\|AX - Y\|_2^2) \quad (8)$$

Even though the unbounded least-squares estimation method in Eq. (8) may be computationally efficient as compared to other methods (e.g., sparsity enhancing estimation methods), it may prove non-robust under certain conditions when the imaged object deviates from the assumed imaging model in Eq. (7). Examples of such deviations are scatterers outside the region of interest (or scatterers outside the grid), point scatterers not aligned with grid intersections, reverberations and dispersion in the imaged object, and non-stationary noise. To improve the performance of the estimation algorithm in (8), a weighted least-squares may be used instead as shown in Eq. (9), where the less accurate observations $y_i$ of the received vector Y are weighted to produce smaller effect on the estimation of X.

$$\hat{X}_{N_x N_z \times 1} = \underset{X}{\operatorname{argmin}}\left(\sum_{k=1}^{N_C N_S} w_k \varepsilon_k^2\right), 0 \leq w_k \leq 1 \quad (9)$$

Another way to improve the performance of the estimation method in (8) is to use a bounded least-squares estimation method where the estimates of the reflectance coefficients are bounded to some region [a,b] as shown in Eq. (10). For example, the estimated reflectance coefficients may be bounded to positive values from zero to one.

$$\hat{X}_{N_x N_z \times 1} = \underset{X \in [a,b]}{\operatorname{argmin}}(\|AX - Y\|_2^2) \quad (10)$$

Figure 4A:
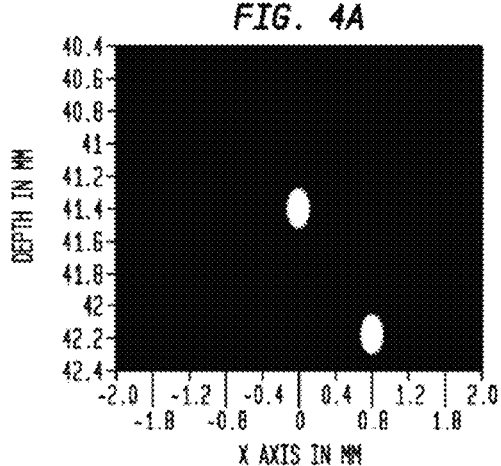
FIGS. 4a-4c illustrate a comparison of the estimated images using two receive channels, where 4a shows the actual reflectivity pattern, 4b shows the estimated image using least squares without bounds, and 4c shows the estimated image using least squares with bounds.
Figure 4B:
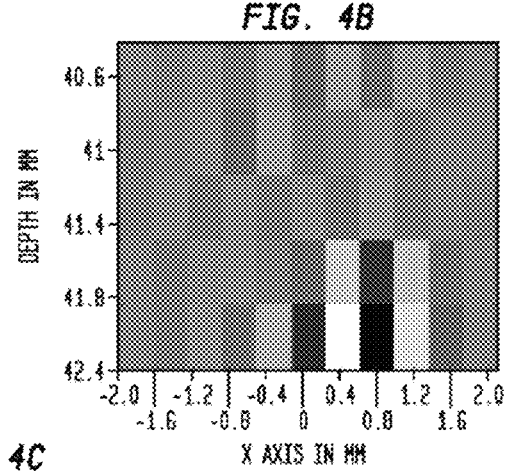
Figure 4C:
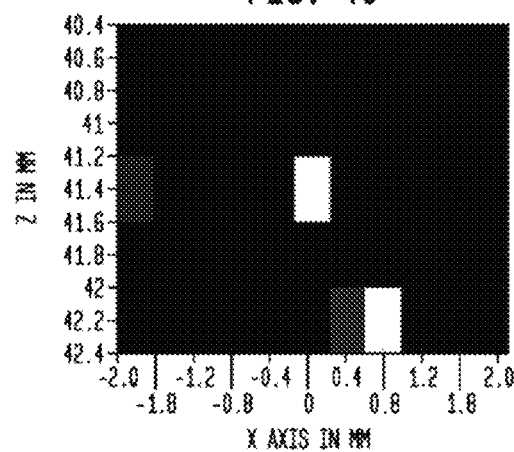

The discussion below and FIG. 4 illustrate that bounded least squares method is a preferred technique for estimation of the image coefficients in X when compared to the case of unbounded least squares.

Lastly, further improvement in the reflectance coefficients estimation may be achieved by using an additional L1-norm in the cost function as shown in Eq. (11), where the weighting coefficient $\lambda$ is a regulation parameter. This estimation method takes advantage of sparsity in scatterer distribution in typical ultrasound images and is known as LASSO estimation method, [39].

$$\hat{X}_{N_x N_z \times 1} = \underset{X \in [a,b]}{\operatorname{argmin}}(\|AX - Y\|_2^2 + \lambda \|X\|_1) \quad (11)$$

The sensing or imaging matrix A is typically bandlimited (or sparse in 2-D frequency domain) and can be 'compressed' to a smaller rank matrix without losing too much of the information available in RF data (echoes). Therefore, in another embodiment described in this patent specification, the sensing or imaging matrix A can be obtained by compressing the RF data (echoes) from $N_C$ transducer channels each taking $N_S$ samples to a fewer number of samples as described below. For each point in the grid at the location $(x_i, z_j)$ the RF signal from $N_C$ transducer elements of the ultrasound probe is either pre-calculated or experimentally determined forming a matrix $B_{ij}$ of the size $N_C$ by $N_S$, where $N_S$ is the total number of samples received by one transducer element (note that each grid point will have different matrix B unique to that grid point). The corresponding column $\tilde{A}^k$ of the imaging matrix A is then formed by compressing matrix $B_{ij}$ with the use of a linear operator $\mathcal{L}$ as shown in Eq. (12), where the column vector $\tilde{A}^k$ is of size $\tilde{N} \times 1$ ($\tilde{N} \leq N_C N_S$).

$$\tilde{A}_{\tilde{N} \times 1}^k = \mathcal{L}\{B_{N_C \times N_S}^{ij}\} \quad (12)$$

Figure 3:
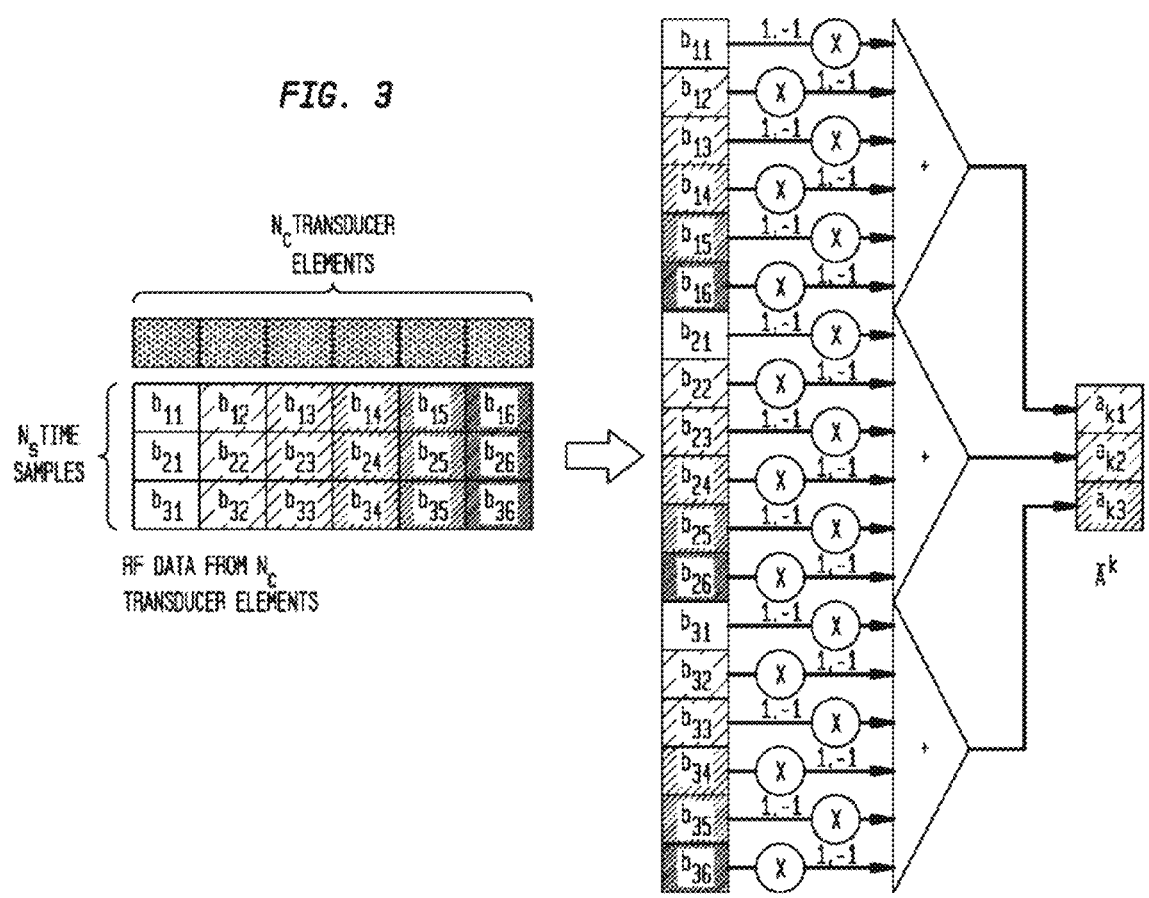
FIG. 3 illustrates an example of creating columns of sensing or imaging matrix A by compressing RF data matrix $B_{ij}$ by projecting the rows of $B_{ij}$ onto a random vector of positive 1's and negative 1's.

This reduces the size of the estimation problem and associated computational costs. An example of the RF data compression and formation of one column vector of the compressed imaging matrix A is shown in FIG. 3. As shown in the figure, the rows of the RF data matrix $B_{ij}$ are projected onto a pseudo-random vector of 1's and −1's of size $N_C \times 1$ (i.e., each sample $a_{km}$ of the column vector $\tilde{A}^k$ is calculated as an inner product between an $m^{th}$ row of $B_{ij}$ and $m^{th}$ pseudo-random vector of 1's and −1's). Note that the pseudo-random vectors can be different for each row of $B_{ij}$.

Simulation results described below have confirmed the theoretical explanation given above for the new approach to super-resolution ultrasound imaging. Simulation were set up with the help of the open source Acoustics toolbox from k-wave [32] along with MATLAB (Mathworks Inc, Natick Mass.). A two-dimensional (x-z) grid was set up in a simulated object or medium with properties similar to homogeneous tissue (c=1540 m/s and density=1000 kg/m³). The simulated scatterers were placed at a depth close to 5 cm. The simulated excitation signal consisted of a 5-cycle sinusoid with center frequency 1.875 MHz, windowed by a Gaussian profile to mimic the signal emitted from a transducer such as 102 (FIG. 1) upon excitation. In this example the technique uses plane wave excitation, and no apodization or focusing was applied on either transmit or receive. The acoustic source (such as transducer 102 in FIG. 1) used for simulations was assumed to have 48 active elements on transmit and 2 active elements on receive. Using one channel alone may be sufficient for imaging in 1-D but for 2-D imaging, at least two receive channels (such as for example the two end elements of transducer 102) are desirable so as to provide accurate estimations in the presence of system noise. In case of 2-D imaging, the signal received by one element of the array of transducer elements from a scatterer such as 106a at one depth may appear the same as the signal received from a different scatterer at another point that lies on the arc intersecting the first point. As such, a better estimate will be provided if at least two transducer channels (elements of transducer 102) are used to track the point scatterer 106a in the medium.

In the simulation examples, firstly the impulse response of each point in a grid of size Nx=11 and Nz=5 was stored in computer memory. For simplicity, uniform grid spacing of 0.4 mm was considered even though the algorithm used in the simulation does not require uniform grid spacing in both dimensions. Next, an object (phantom) consisting of scatterers of higher density and acoustic speed than the surrounding medium was excited using the aforementioned transducer and excitation signal. The phantoms were constructed as disc structures with an acoustic speed of 3000 m/s. After receiving the echoes (RF data), image reconstruction was performed using the bounded least squares estimation equation shown in Eq. (10) with bounds from zero to one.

The importance of using least squares with bounds is shown in FIG. 4, where the figures show a comparison between unbounded and bounded least squares estimation. The columns of the imaging matrix A are highly correlated and as a result any response from the phantom that is not perfectly aligned with one of the columns of the matrix A will have non-zero projections onto more than one column vector of the matrix A. For example, if the scattering point of the phantom is located off the grid, its response will project not only onto the impulse response from the nearest neighbors, but rather onto impulse responses from a large neighborhood. As a result, similar to the linear deconvolution methods the decoded image with unbounded least-squares estimation exhibits widely spread point spread function indicating poor resolution.

Figure 5A:
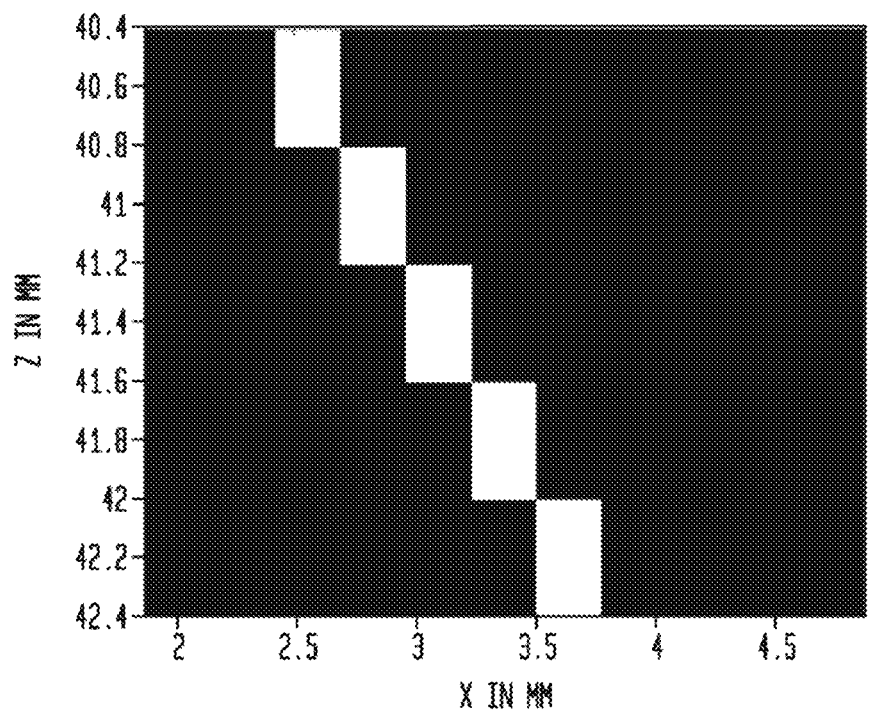
FIGS. 5a and 5b show simulation results using a diagonal row of scatterers, where 5a is an actual reflectivity pattern and 5b is the estimated image using bounded least squares and two receiving channels.
Figure 5B:
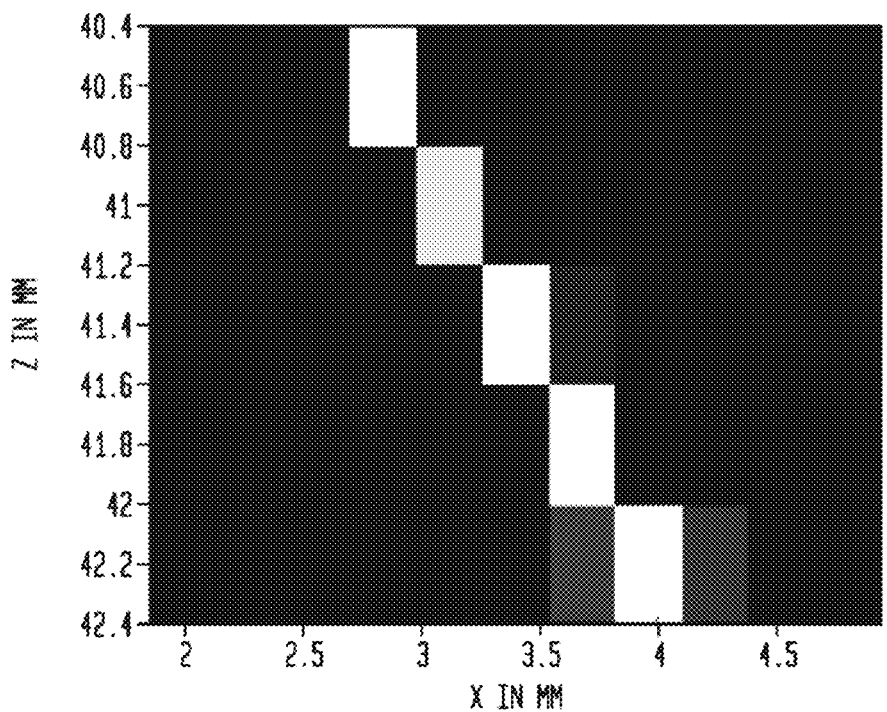

Super-resolution can be achieved if the conditions of positivity and compactness are met [30], which is why the images estimated using bounded least squares achieve super-resolution. Additional simulations were run for increasing number of point scatterers 106a and various patterns confirming that least squares estimation with bounds as described in this patent specification provides a good estimate of the target phantom (object) provided at least two channels (elements of transducer 102) are used. FIGS. 5a and 5b show the estimated image of a diagonal line of scatterers (FIG. 5(b)) in comparison to the actual reflectivity pattern (FIG. 5(a)). Here two receive channels were used for decoding.

Figure 6A:
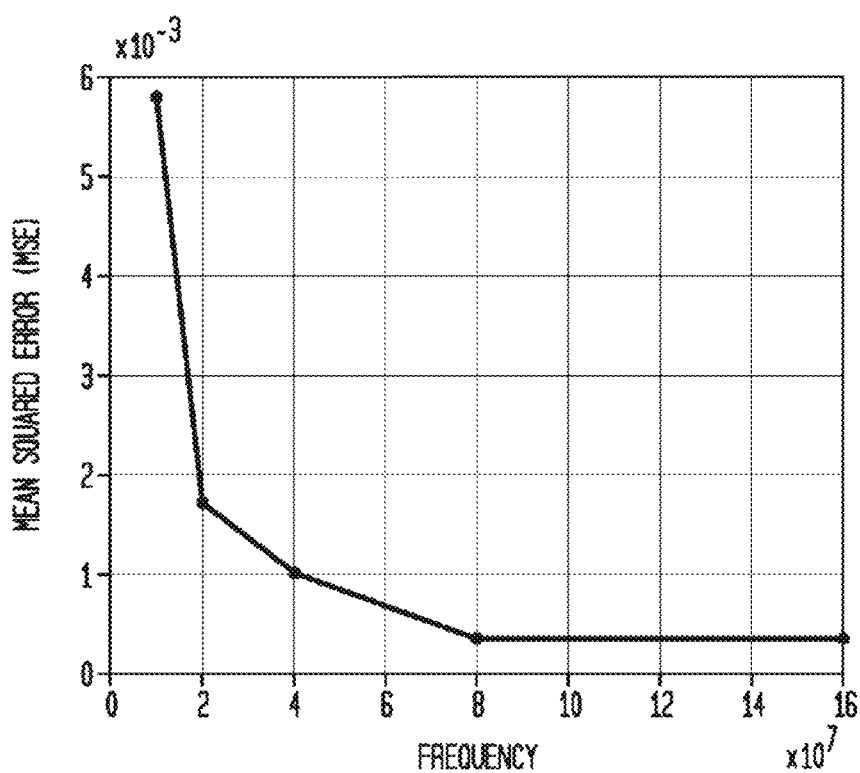
FIGS. 6a and 6b are plots showing mean squared error vs (6a) frequency (6b) number of excitation cycles.
Figure 6B:
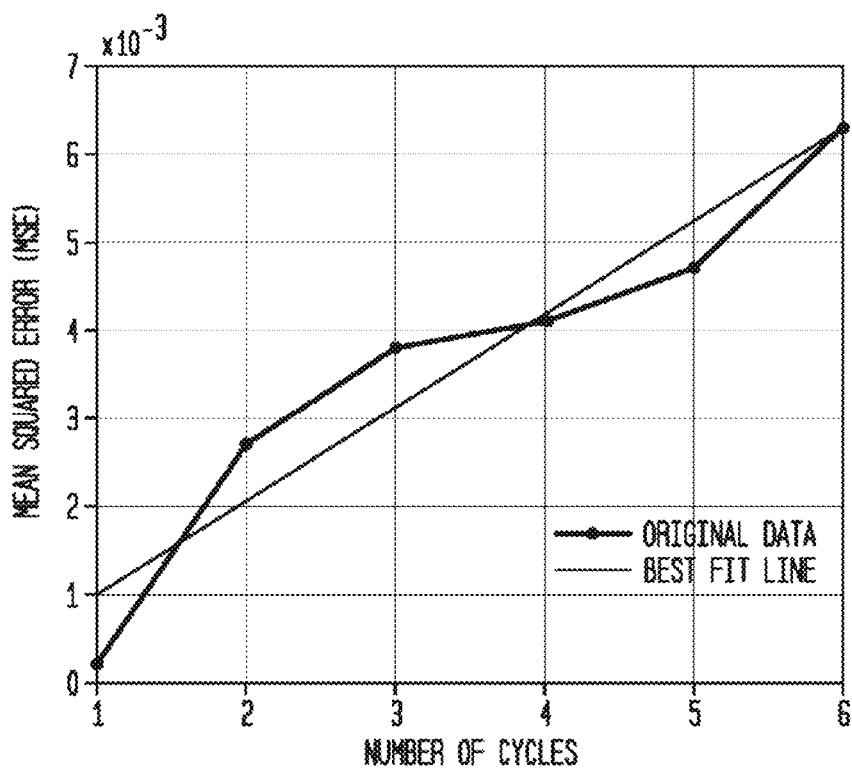

Further simulations were run with an increasing number of receiving channels. In the absence of noise, adding more than two channels did not provide substantial improvement to image reconstruction quality for the setup used in the simulations. Still other simulations were run to investigate the effects of grid size and change in frequency on the image reconstruction. The results shown in FIG. 6(a) indicate that increasing the frequency for a grid size of 0.4 mm at a given depth of 4.86 cm decreases the mean squared error (MSE) of the estimated images. At frequency of 8 MHz and 16 MHz, the error starts to flatten out since attenuation starts becoming prominent. From simulations, we see that excitation frequency and grid spacing (dx, dz) follow the same error trend. For example, reducing the frequency by a factor of two is similar to reducing the grid size by a factor of two. As shown in FIG. 6(b), the MSE also increases with increasing number of cycles in the excitation signal which goes hand in hand with the fact that resolution decreases as the spatial pulse length increases where spatial pulse length is the product of number of cycles and excitation wavelength.

Figure 7A:
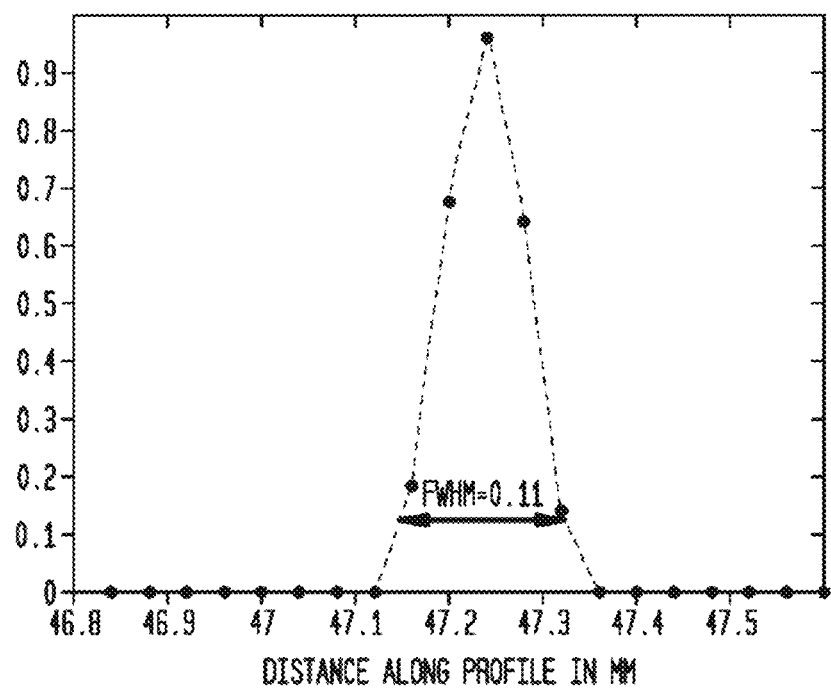
FIG. 7a shows an Axial Point Spread Function and FIG. 7b shows a Lateral Point Spread Function.
Figure 7B:
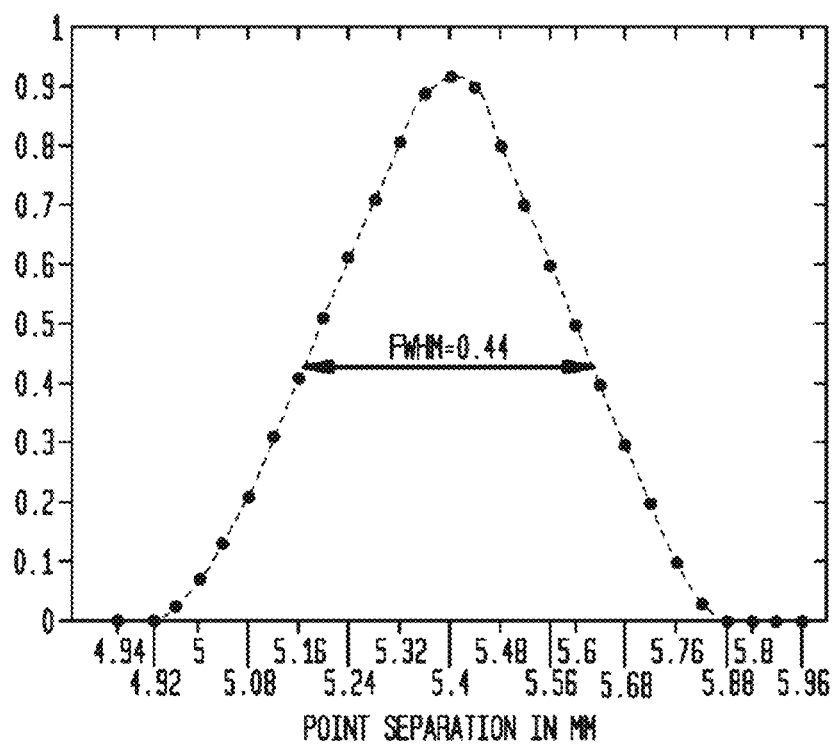

FIGS. 7a and 7b shows the point spread function (PSF) of the simulated ultrasound system by sweeping over a point in the axial direction. The axial PSF has a full width half maximum (FWHM) of 0.1264 mm at the excitation frequency of 1.865 MHz. The lateral PSF has a wider profile as expected, indicating lower resolution compared to axial resolution. The lateral PSF has a FWHM of 0.436 mm.

Experimental results further confirmed the new approach described in this patent specification. Experiments were performed using Verasonics V1 ultrasound scanner (Verasonics, Inc. Kirkland Wash. 98034) connected to a 96-channel phased array ATL probe, P4-1 (ATL Ultrasound, Inc., Bothel Wash. 98041). Only the first half of the aperture (48 channels) was used for transmission while two channels from the same aperture are used on receive. Only the first half of the transducer aperture (14.16 mm of total aperture size of 28 mm) was used on transmission, to ensure imaging in the far field region while maintaining a sufficiently high signal to noise ratio (SNR). As in the simulations, only two channels were used on receive to uniquely recover the 2-D target. The ultrasound phantom consisted of fishing wires in a tank filled with degassed water. The fishing wires are made of nylon and are of 0.2 mm in diameter. The probe was placed perpendicular to and roughly 8.9-9.2 cm above the fishing wires. The excitation frequency was set to 1.875 MHz corresponding to a wavelength of 0.833 mm for acoustic speed of 1540 m/s. Raw RF data (echoes) was collected and then passed through a FIR bandpass filter in MATLAB which removes noise outside the bandwidth of interest. This was followed by the image reconstruction algorithm. No apodization, focusing and beamforming were applied. The grid size used for the experiments was similar to the dimensions in the simulation setup and was large enough to cover the phantoms used for the experiments.

The experiments used were done in two-dimensions i.e. the x-z plane as illustrated in FIG. 1, as extension to 3 dimensions can be achieved by extending grid 106 (in FIG. 1) to 3D space. The sensing or imaging matrix A was populated using a simple Nz=5, Nx=11 grid spanning 2 mm axially and 4.4 mm laterally, where each grid intersection represented a point scatterer. The grid points were taken 0.4 mm apart in the axial and lateral directions.

Figure 8A:
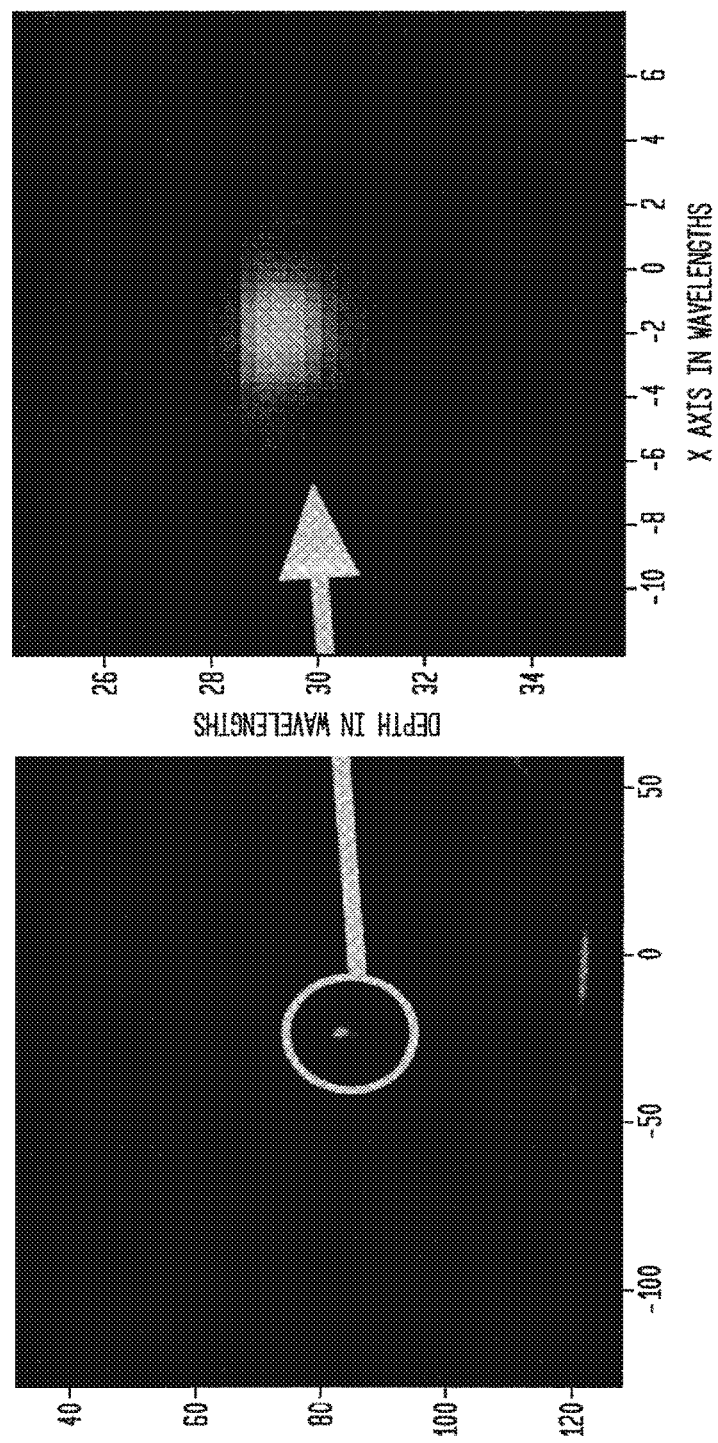
FIGS. 8a, 8b, and 8c illustrate experimental results for an object with two wires separated by 0.8 mm laterally, where 8a shows a conventional B-mode ultrasound image of the object with the wires on left and a magnification of the wire image at right, 8b and 8c show magnified images of the wires using the imaging technique described in this patent specification, at one location in 8b and at another location in 8c.
Figure 8B:
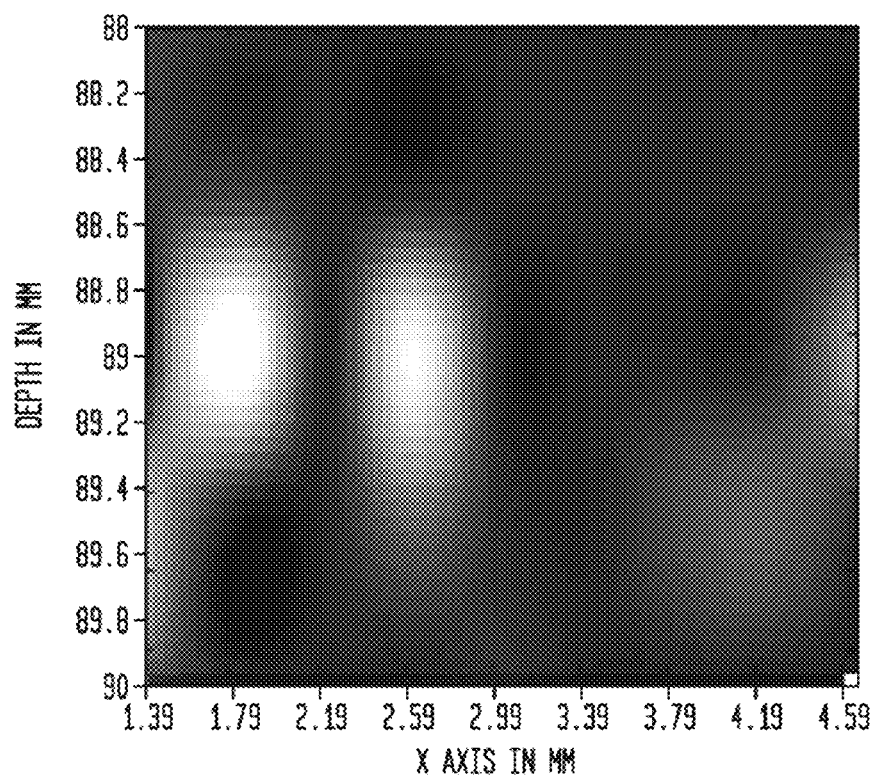
Figure 8C:
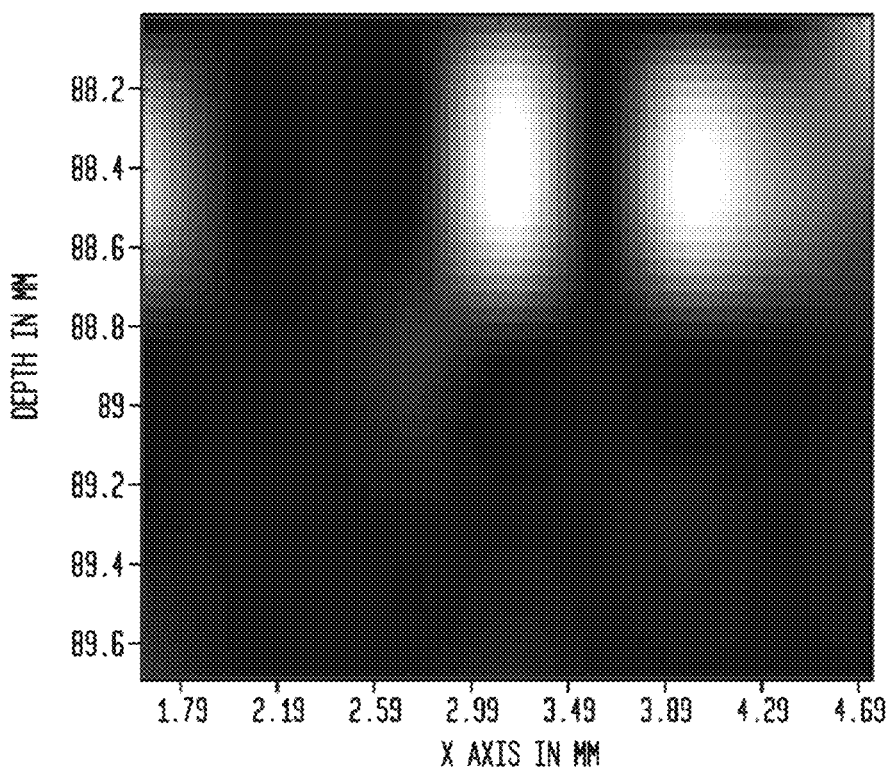

The first two-dimensional image involved two fishing wires separated by 0.8 mm laterally. The results are shown in FIGS. 8a, 8b, and 8c, where 8a shows a conventional B-mode ultrasound image of the object with the wires on left and a magnification of the wire image at right, and 8b and 8c show magnified images of the wires using the imaging technique described in this patent specification, at one location in 8b and at another location in 8c. Some background noise is visible in the images and can be reduced by averaging the reconstructed images. Note that the axes of the magnifications of the conventional ultrasound images shown in the figures are units of wavelength.

Figure 9A:
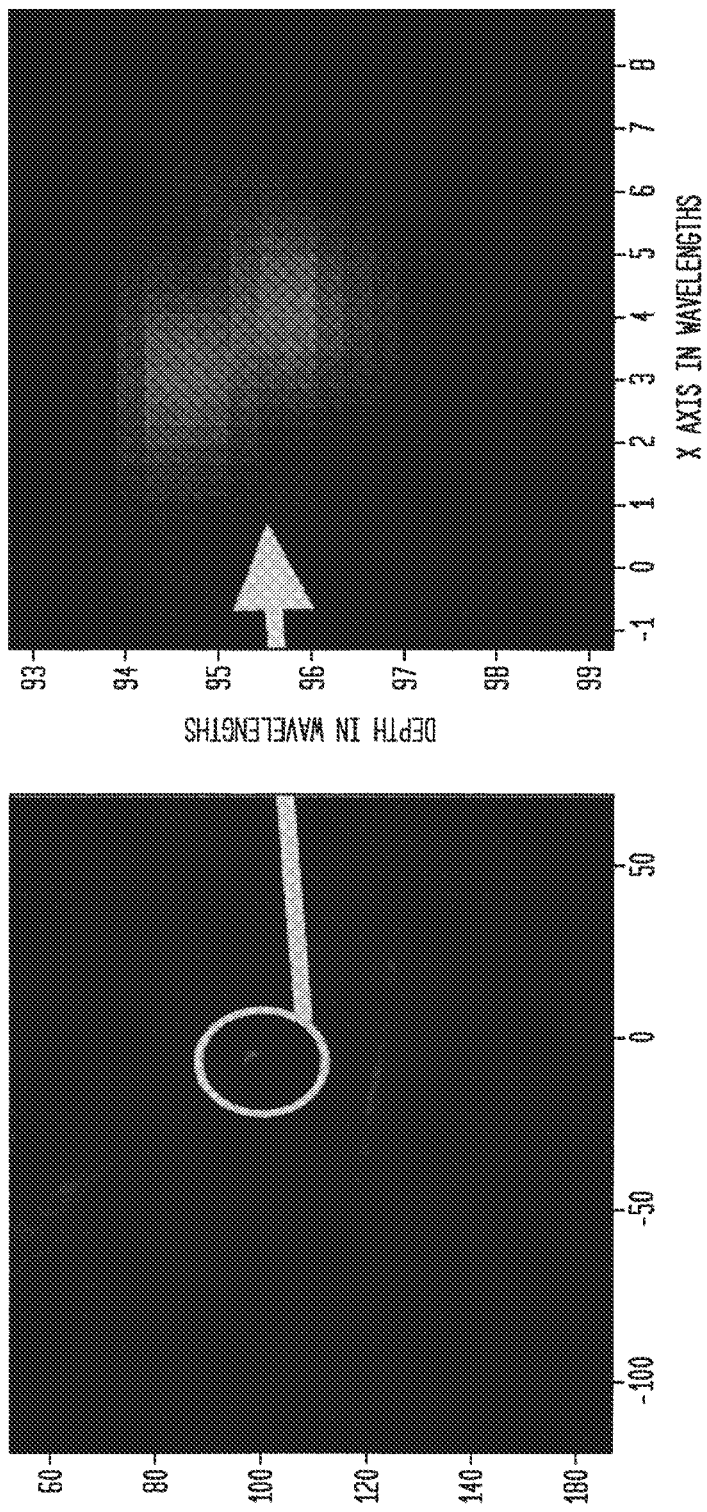
FIGS. 9a, 9b, and 9c illustrate additional experimental results for an object with two wires separated by 0.8 mm laterally and axially, where 9a shows a conventional ultrasound image of the object with the wires on left and a magnification of the wire image at right, 9b shows an interpolated image of the two wires separated by 0.8 mm using the new approach described in this patent specification, and 9c shows the wires at a different location.
Figure 9B:
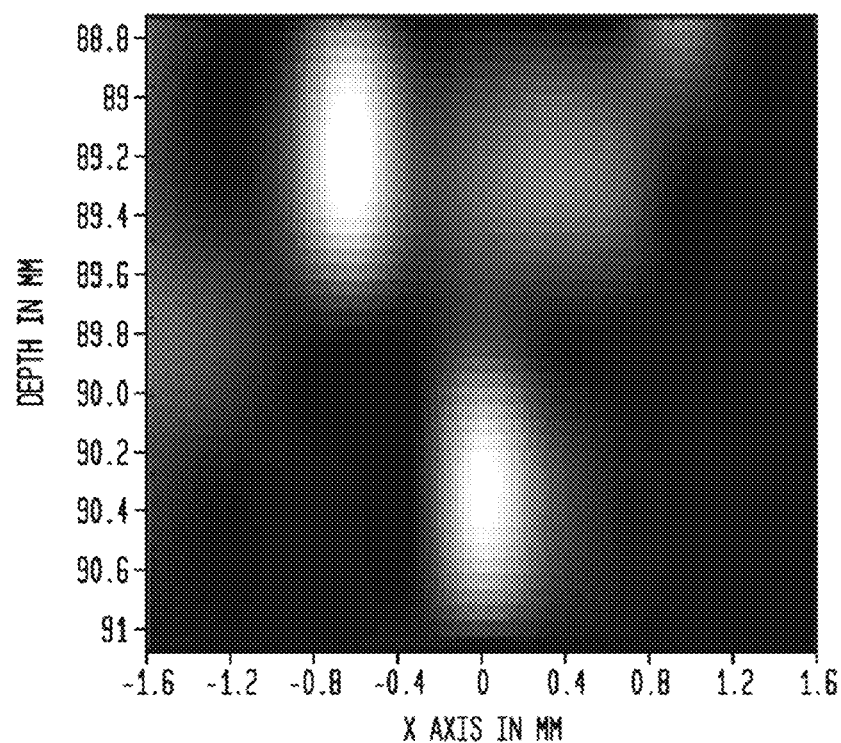
Figure 9C:
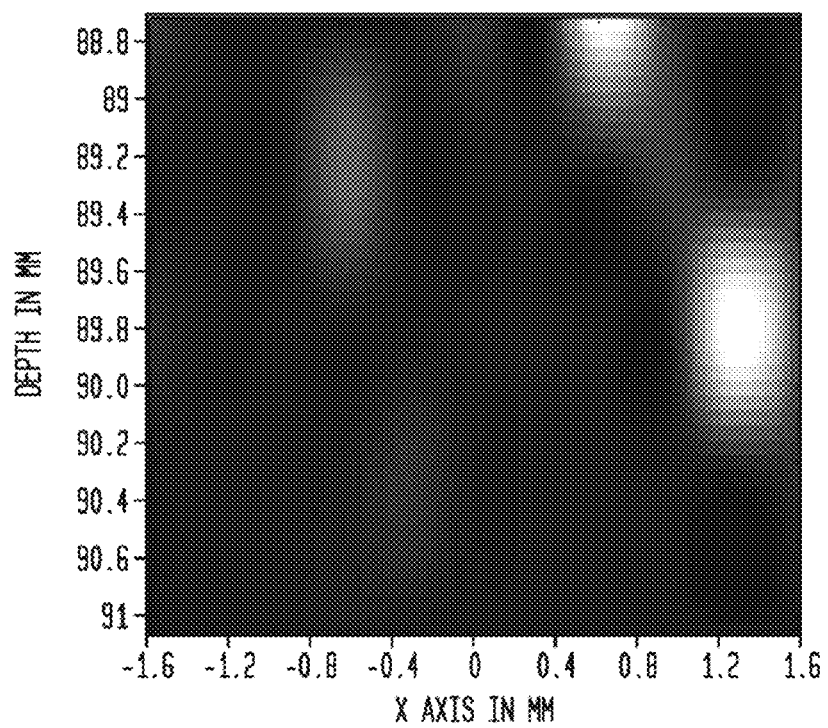
Figure 10A:
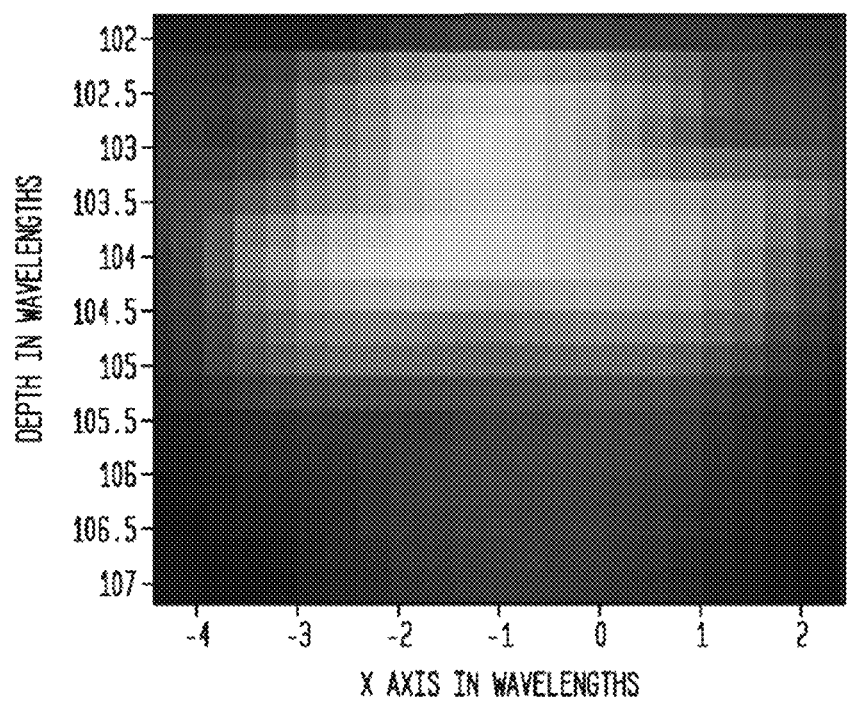
FIGS. 10a, 10b, 10c, and 10d shows results of an experiment where fishing wires are placed randomly: 10a shows a magnification of a conventional ultrasound image with three wires, 10b shows an image of the three wires produced as described in this patent specification, 10c shows a magnification of four wires in a conventional ultrasound image, and 10*d* shows an image of the four wires produced with the new approach of this patent specification.
Figure 10B:
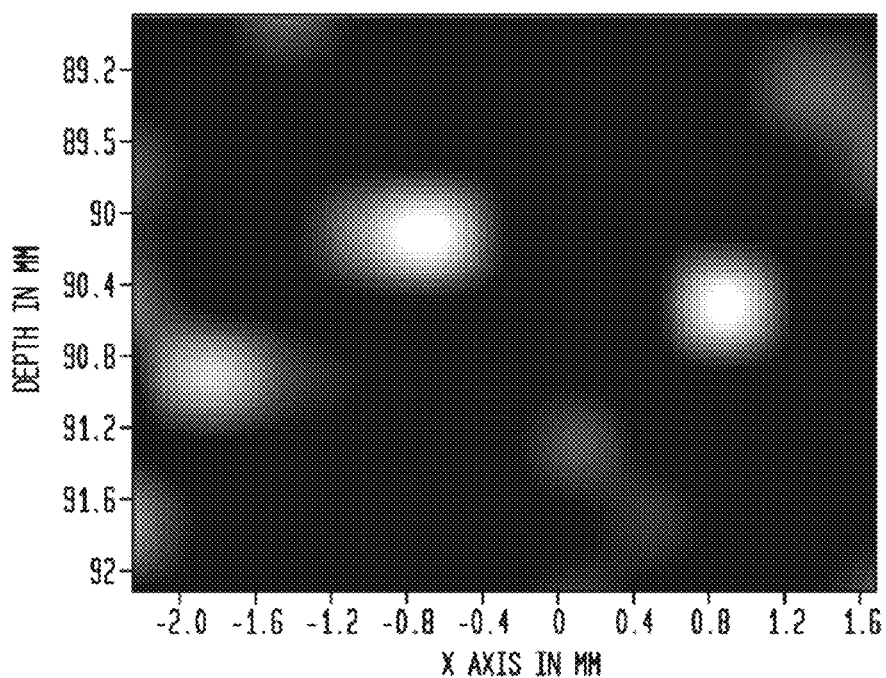
Figure 10C:
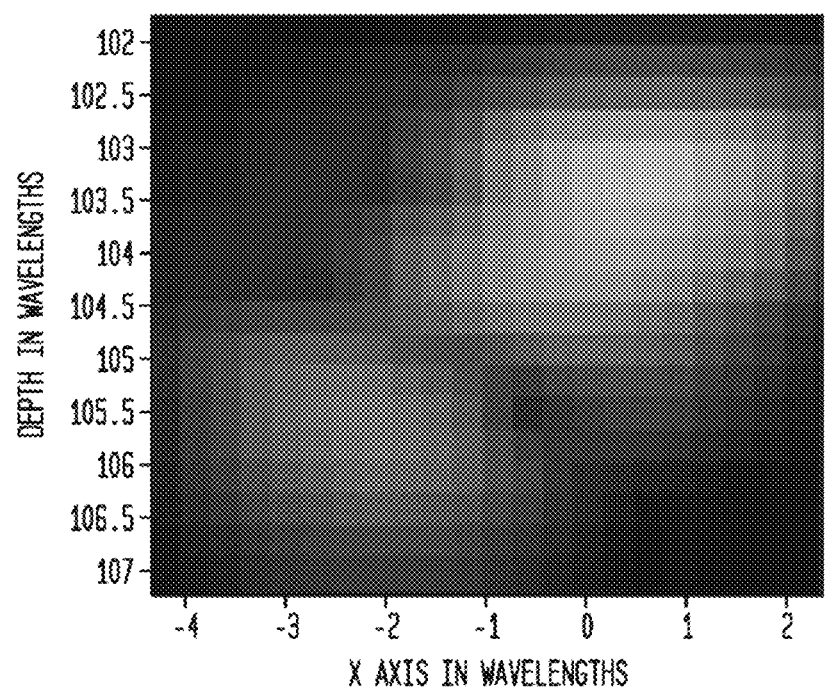
Figure 10D:
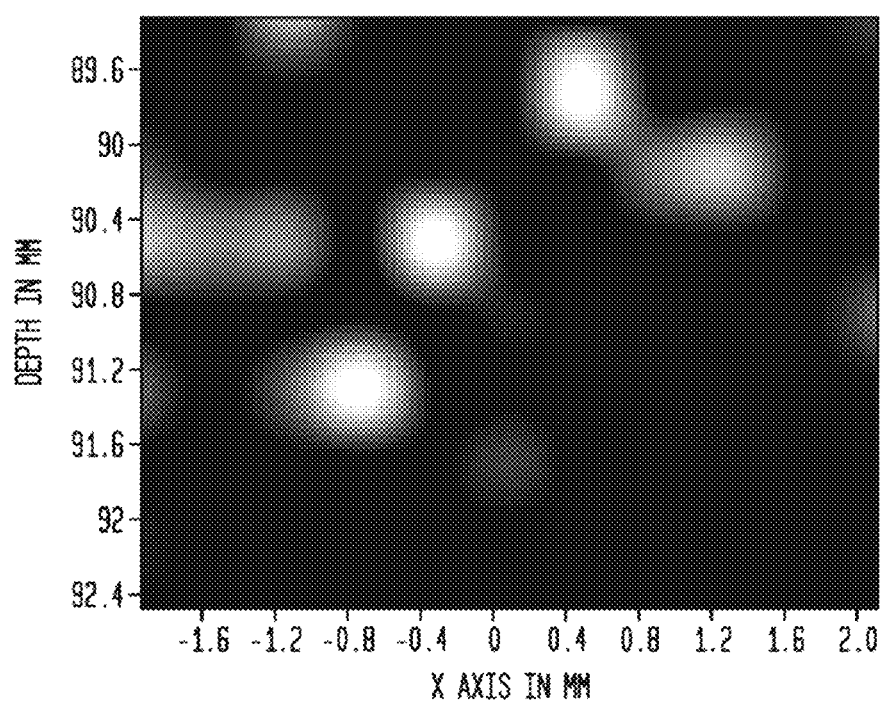

FIGS. 9a, 9b, and 9c illustrate additional experimental results for an object with two wires separated by 0.8 mm laterally and axially, where 9a shows a conventional ultrasound image of the object with the wires on left and a magnification of the wire image at right, 9b shows an interpolated image of the two wires separated by 0.8 mm using the new approach described in this patent specification, and 9c shows the wires at a different location.

FIGS. 10a, 10b, 10c, and 10d shows results of an experiment where fishing wires are placed randomly: 10a shows a magnification of a conventional ultrasound image with three wires, 10b shows an image of the three wires produced as described in this patent specification, 10c shows a magnification of four wires in a conventional ultrasound image, and 10d shows an image of the four wires produced with the new approach of this patent specification. Additional imaging was done of three and four wire phantoms using a 9×11 (Nz=9, Nx=11) grid which spanned 3.6 mm axially and 4.4 mm laterally. The area outlined in the box in FIGS. 10a and 10c approximates the area shown in FIGS. 10 (b) and (d) respectively.

Figure 11A:
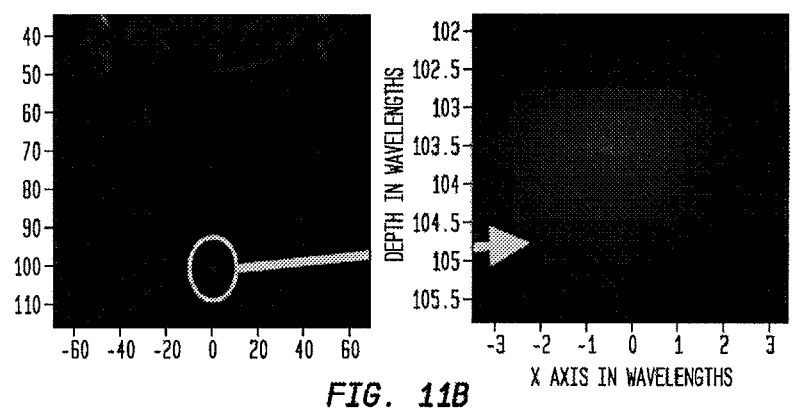
FIGS. 11*a* and 11*b* illustrate further experimental results: 11*a* shows a conventional ultrasound image of two wires separated by 0.8 mm passing through beefsteak (full image on left and magnification on right)
Figure 11B:
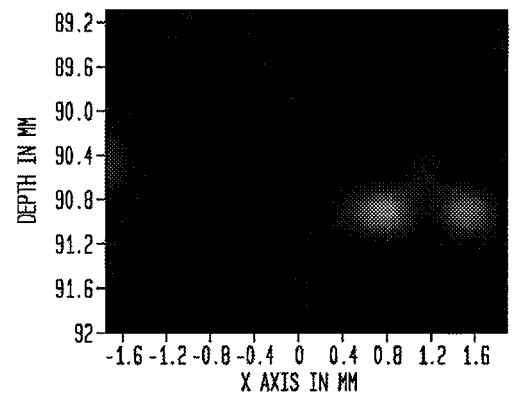

FIGS. 11a and 11b illustrate further experimental results: 11a shows a conventional ultrasound image of two wires separated by 0.8 mm passing through beefsteak (full image on left and magnification on right) and FIG. 11b shows an image of the same object produced with the new approach described in this patent specification. The speed of sound in water is roughly 1540 m/s and has an acoustic impedance of 1.483 g/cm$^2$ sec×10$^5$ and density equal to 1 g/cm$^3$. Acoustic waves get reflected or refracted at boundaries between objects with different acoustic properties. For a real-life ultrasound imaging scenario, an experiment was performed to see the resolution capability of the technique behind living tissue. This was performed using a piece of steak of 1 cm thickness. Beef has an acoustic impedance of 1.68 g/cm$^2$ sec×10$^5$ and density of 1.08 g/cm$^3$. As can be seen in FIG. 11b, the signal is attenuated due to the tissue layer above the wires while the resolution is clearly maintained.

Figure 12A:
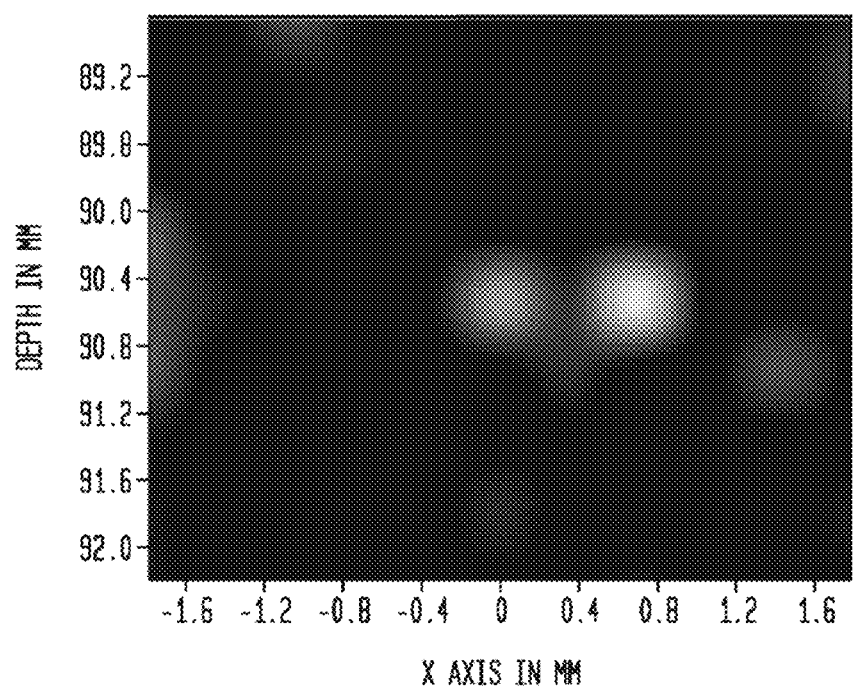
FIG. 12*a* shows further experimental results using the new approach described in this patent specification on the same object (two wires separated by 0.8 mm in a beefsteak): 12*a* shows a single frame image
Figure 12B:
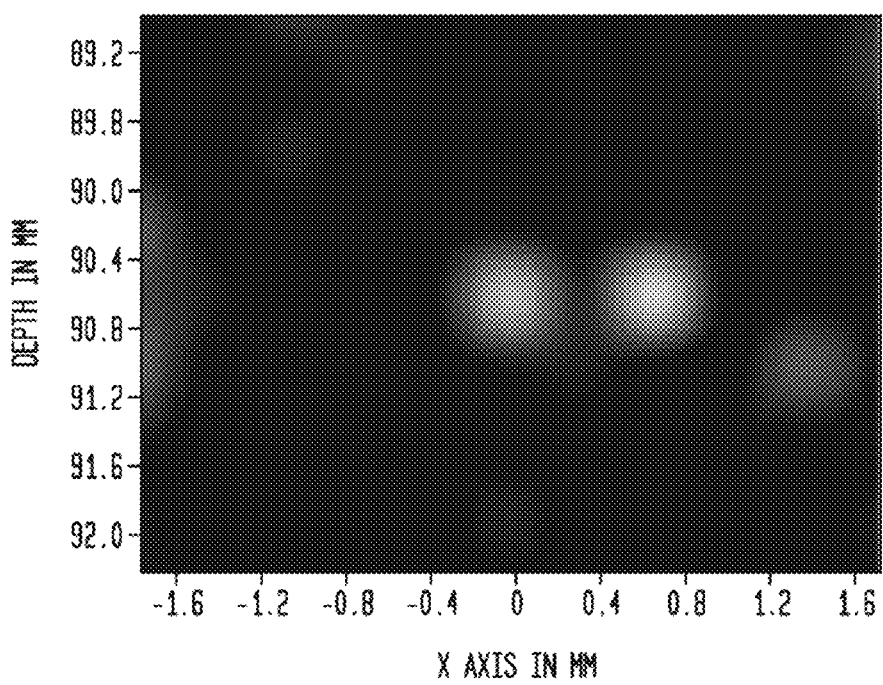
FIG. 12*b* shows an averaged image, over several frames.

FIG. 12a shows further experimental results using the new approach described in this patent specification on the same object (two wires separated by 0.8 mm behind a beefsteak): 12a shows a single frame image and FIG. 12b shows an averaged image, over several frames. The images presented before FIGS. 12a and 12b were not averaged. In order to reduce the noise present in the estimated images, averaging over multiple frames has proven to help. FIG. 12b shows the estimated image from the experiment with steak after 15 averages in comparison to a single frame of the image.

Figure 13:
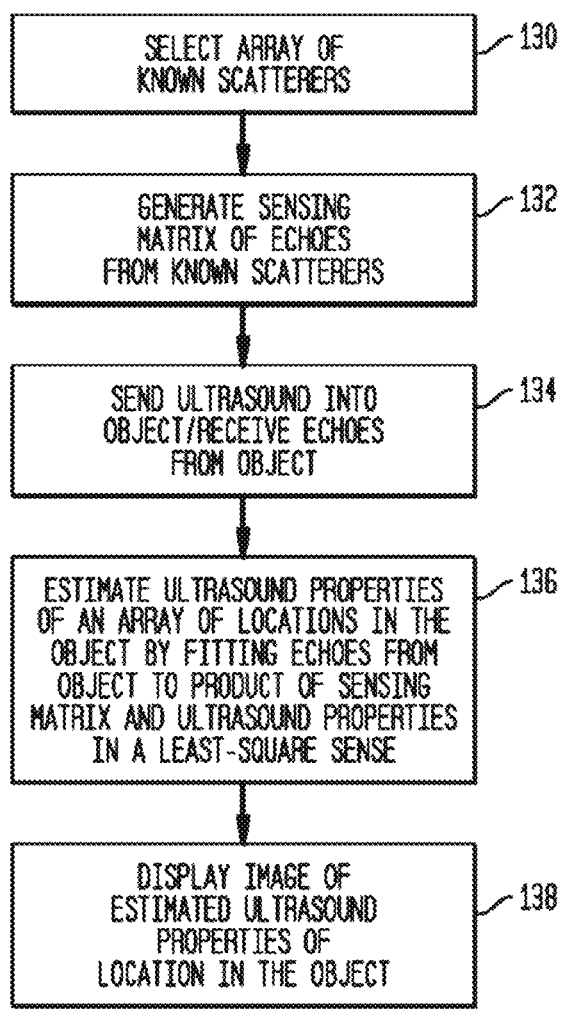
FIG. 13 illustrates main steps of an example of estimating ultrasound properties of locations in an object.

FIG. 13 illustrates main step of a process for estimating ultrasound properties of locations in an object according to the above description. In step 130 the process selects an array of known scatterers. In a simplified example, the known scatterers can be high-density point scatterers in water or fat. In step 132, the process generates a sensing matrix by calculations, with or without deriving actual echoes of the known scatterers by ultrasound measurements. In step 134, the process sends ultrasound into the object and receives echoes as described above, and in step 136 fits the received echoes to a combination such as a product of the sensing matrix and a vector of ultrasound properties of locations in the object. The fitting process in step 136 may be performed by finding ultrasound properties of locations in the object that minimize fitting error in a least-square sense.

Figure 14:
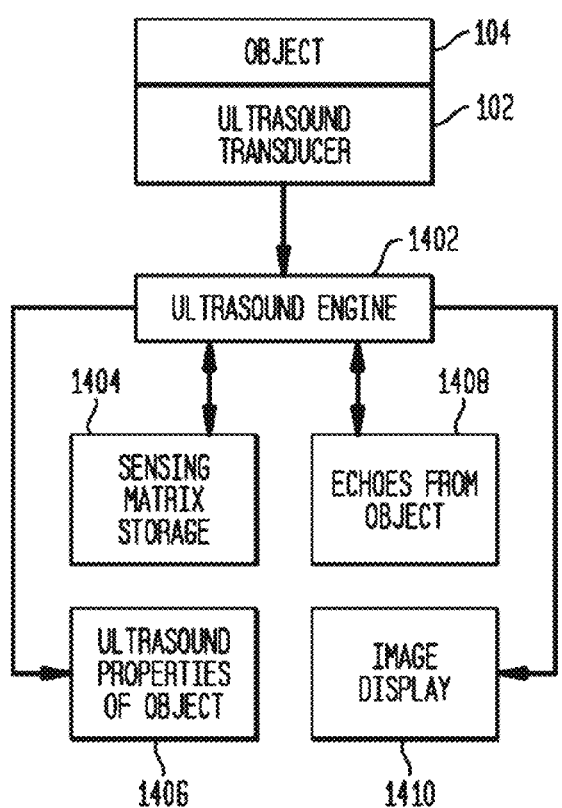
FIG. 14 is a block diagram of a system for estimating ultrasound properties of locations in an object.

FIG. 14 illustrates a block diagram form of a system for carrying out the estimation of ultrasound properties of locations in an object using the processes described above. Ultrasound transducer 102 sends ultrasound into object 104 and receives echoes from the object as described above. An ultrasound engine 1402, which can be the engine of a conventional processor such as in the examples given in the background section of this patent specification, controls transducer 102 and processes the echoes received from the transducer by carrying out the processes described above, using programming that a person of ordinary skill in programming can implement based on the description and equations explained in this patent specification. Computer storage 1404 stores the sensing matrix (based on the known array of scatterers). Computer storage 1406 stores the initial values of ultrasound properties of locations in the object before the fitting process and their modified values that result from fitting echoes from the object, which are stored in computer storage 1408, to the combination such as a product of the sensing matrix and a vector of ultrasound properties of locations in the object. From the above-described fitting, ultrasound engine 1402 estimates ultrasound properties of locations in object 104 and displays them as an image or in another form on image display 1410.

In certain application, alternative embodiments of the ultrasound transmitting and receiving transducer elements may offer important benefits. One example is imaging the brain through the skull and another is non-destructive testing of object with irregular surfaces. It has been found that when imaging the brain, ridges in the skull that typically are at the sutures of the scull bones or at protuberances, lines or crest of the skull structure, can interfere with the transmitted and/or received ultrasound imaging signals and cause image artifacts. Irregular surfaces of objects can present similar challenges in non-destructive testing, for example of turbine blades.

In the embodiments described above in this patent specification, all of the elements of a transducer array, for example all 48 elements, can be driven to transmit imaging ultrasound energy into the patient or object being imaged, but less than all, for example, only two, can be used to receive ultrasound energy (echoes) for imaging. However, not all the transducer elements need be used to transmit. For example, if the transducers are in a linear or curved array, and there is a total of 48 transducer elements available to transmit, a few of these elements that are over or near a ridge at a suture of scull bones can be disabled so they do not transmit an ultrasound pulse that the remaining transducer elements transmit. The number of transmitting elements can still be greater than the number of elements that receive reflections of the transmitted pulse, but image artifacts can be significantly reduced by disabling or not driving the transmitting elements that are over or near a structure such a ridge.

Figure 15:
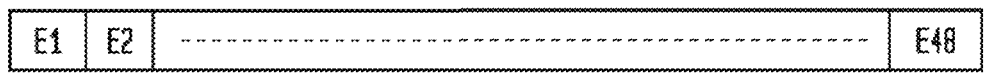
FIG. 15 illustrates in schematic form an ultrasound transducer having a row of transducer elements.

FIG. 15 illustrates a transducer array 102 of 48 elements E1 through E48 arranged in a line that can be straight or can be curved to better conform to a generally round object such as the skull. In one example, all 48 elements E1 through E48 can be driven to emit an ultrasound pulse, and the fewer of those elements, such as 2 (or 3, 4, etc.) are used to receive echoes of the transmitted pulse. In an alternative embodiment, not all 48 elements transmit—for example elements E30 through E35, which are over a ridge in a skull or a surface irregularity of an object, are disabled (not driven) so only elements E1-E29 and E36-E48 transmit ultrasound into the skull or object. Only a single element may be disabled in some examples. Transducer array 102 may comprise a single line of transduce elements or can be a two-dimensional array of two or more lines of transducer elements and can have any practical number of transducer elements. The same transducer elements can be used to transmit ultrasound and then receive echoes, or one set of transducer elements can be used only to transmit ultrasound and another only to receive echoes. In all cases, the treatment and processing of the echoes can be as discussed in detail above.

Figure 16:
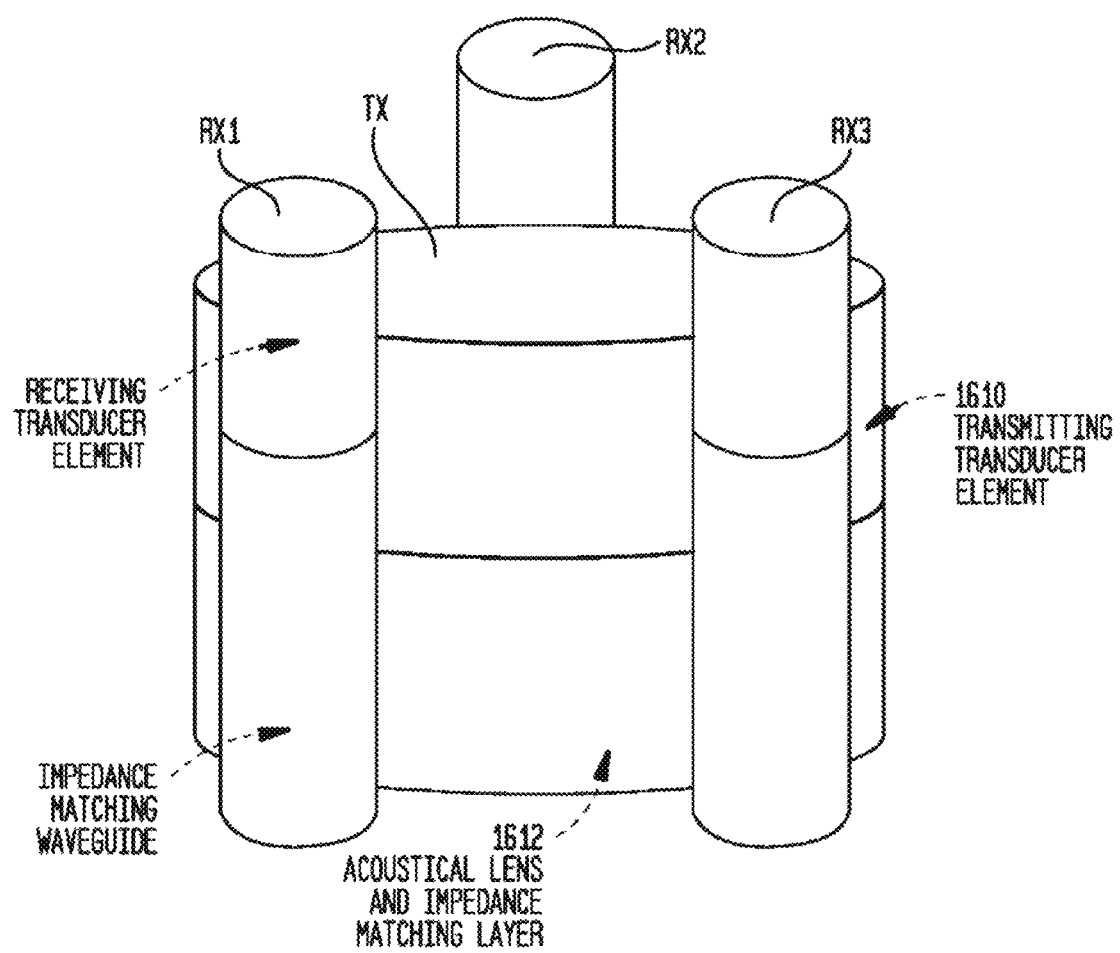
FIG. 16 illustrates sending and transmitting elements of an ultrasound transducer suited for use in some applications of an ultrasound system according to certain embodiments.

FIG. 16 illustrates another embodiment that can be particularly suitable when a smaller volume of a patient's body or of an object is of interest, or when the surface with which the transducer makes acoustic contact precludes or makes difficult the use of the ultrasound transducer arrays discussed above. In the example of FIG. 16, a single transmitting transducer element 1610 is driven to transmit ultrasound pulses into a patient's tissue or into an object, preferably through an acoustical lens and impedance matching layer 1612 that help confine the ultrasound energy from element 1610 to a beam of a desired shape that can be primarily directed to a volume of particular interest in the patient or the object. Several receiving transducer elements RX1, RX2, and RX3 surround transmitting element 1610 to receive echoes of the ultrasound energy that transmitting element 1610 sends into the patient or object. Preferably, each receiving element receives echoes through a respective impedance matching waveguide as shown. Although three receiving elements are illustrated, only two or more than three can be used in some embodiments. Similarly, although a single transmitting element 1610 is illustrated, two or more transmitting elements can be used in place of element 1610, for example two or more of the elements of a conventional transducer array in which the remaining elements are not used to transmit ultrasound, in which can some of the remaining elements of the array can be used as receiving elements or some of the transmitting elements can be used as receiving elements as well.

In operation of the embodiment of FIG. 16, the bottom surfaces of the illustrated impedance matching waveguides and impedance matching layer are pressed into acoustic coupling with a patient or an object, (e.g., through a layer of ultrasound gel). Transmitting transducer element is driven to emit ultrasound pulses that are the same in principle as discussed above for ultrasound engine 1404 of FIG. 14, and receiving elements RX1, RX2, and RX3 produce echo signals that in principle are the same as in the embodiment of FIG. 14. One difference is that transmitting transducer element 1610 typically is larger than any individual element or an array such as array 102 of FIG. 15 so element 1610 can produce an ultrasound pulse that has enough acoustical energy for the volume targeted for imaging. Another difference is that the receiving transducers in FIG. 16 only receive echoes. This can simplify the equipment requirements because when the transmitting and receiving elements are kept electrically isolated, front end electronics would not need the typical high-voltage TX/RX switches to separate transmitting and echo signals from each other. However, as noted above, an alternative is to use as some or all of receiving transducer elements some of the transmitting transducer elements. The echoes from the receiving elements in the embodiment of FIG. 16 and variations thereof are processed into an image in the manner discussed above for the embodiments of FIGS. 1-14.

Although the foregoing has been described in some detail for purposes of clarity, it will be apparent that certain changes and modifications may be made without departing from the principles thereof. It should be noted that there are many alternative ways of implementing both the processes and apparatuses described herein. Accordingly, the present embodiments are to be considered as illustrative and not restrictive, and the body of work described herein is not to be limited to the details given herein, which may be modified within the scope and equivalents of the appended claims.

REFERENCES

[1]. E. J. Candè and M. B. Wakin, "An introduction to compressive sampling," Signal Processing Magazine, IEEE, vol. 25, no. 2, pp. 21-30, 2008.

[2]. E. J. Candes and T. Tao, "Decoding by linear programming," Information Theory, IEEE Transactions on, vol. 51, no. 12, pp. 4203-4215, 2005.

[3]. O. Michailovich and D. Adam, "Phase unwrapping for 2-d blind deconvolution of ultrasound images," Medical Imaging, IEEE Transactions on, vol. 23, no. 1, pp. 7-25, 2004.

[4]. T. Taxt and G. V. Frolova, "Noise robust one-dimensional blind deconvolution of medical ultrasound images," Ultrasonics, Ferroelectrics, and Frequency Control, IEEE Transactions on, vol. 46, no. 2, pp. 291-299, 1999.

[5]. J.-F. Synnevag, A. Austeng, and S. Holm, "Benefits of minimum-variance beamforming in medical ultrasound imaging," Ultrasonics, Ferroelectrics, and Frequency Control, IEEE Transactions on, vol. 56, no. 9, pp. 1868-1879, 2009.

[6]. S. Holm, J. Synnevag, and A. Austeng, "Capon beamforming for active ultrasound imaging systems," in Proc. IEEE, 13th DSP Workshop, 2009.

[7]. J. A. Mann and W. Walker, "A constrained adaptive beamformer for medical ultrasound: Initial results," in Ultrasonics Symposium, 2002. Proceedings. 2002 IEEE, vol. 2. IEEE, 2002, pp. 1807-1810.

[8]. I. K. Holfort, F. Gran, and J. A. Jensen, "P2b-12 minimum variance beamforming for high frame-rate ultrasound imaging," in Ultrasonics Symposium, 2007. IEEE. IEEE, 2007, pp. 1541-1544.

[9]. B. M. Asl and A. Mahloojifar, "Eigenspace-based minimum variance beamforming applied to medical ultrasound imaging," Ultrasonics, Ferroelectrics, and Frequency Control, IEEE Transactions on, vol. 57, no. 11, pp. 2381-2390, 2010.

[10]. C. Quinsac, A. Basarab, J. Gregoire, and D. Kouame, "3d compressed sensing ultrasound imaging," in Proc. IEEE Int. Ultrason. Symp. (IUS), San Diego, USA, 2010.

[11]. C. Quinsac, A. Basarab, J.-M. Girault, and D. Kouamé, "Compressed sensing of ultrasound images: sampling of spatial and frequency domains," in Signal Processing Systems (SIPS), 2010 IEEE Workshop on. IEEE, 2010, pp. 231-236.

[12]. M. Schiffner, T. Jansen, and G. Schmitz, "Compressed sensing for fast image acquisition in pulse-echo ultrasound," Biomedical Engineer-ing/Biomedizinische Technik, vol. 57, no. SI-1 Track-B, pp. 192-195, 2012.

[13]. N. Wagner, Y. C. Eldar, A. Feuer, G. Danin, and Z. Friedman, "Xampling in ultrasound imaging," CoRR, vol. abs/1104.5327, 2011.

[14]. N. Wagner, Y. C. Eldar, A. Feuer, and Z. Friedman, "Compressed beamforming applied to b-mode ultrasound imaging," in Biomedical Imaging (ISBI), 2012 9th IEEE International Symposium on. IEEE, 2012, pp. 1080-1083.

[15]. D. Friboulet, H. Liebgott, and R. Prost, "Compressive sensing for raw rf signals reconstruction in ultrasound," in Ultrasonics Symposium (IUS), 2010 IEEE. IEEE, 2010, pp. 367-370.

[16]. H. Liebgott, R. Prost, and D. Friboulet, "Pre-beamformed rf signal reconstruction in medical ultrasound using compressive sensing," Ultrasonics, vol. 53, no. 2, pp. 525-533, 2013.

[17]. P. Blomgren, G. Papanicolaou, and H. Zhao, "Super-resolution in time-reversal acoustics," The Journal of the Acoustical Society of America, vol. 111, no. 1, pp. 230-248, 2002.

[18]. A. J. Devaney, "1super-resolution processing of multistatic data using time reversal and music," 2000.

[19]. Y. Labyed and L. Huang, "Super-resolution ultrasound imaging using a phase-coherent music method with compensation for the phase response of transducer elements," Ultrasonics, Ferroelectrics, and Frequency Control, IEEE Transactions on, vol. 60, no. 6, pp. 1048-1060, 2013.

[20]. M. A. O'Reilly and K. Hynynen, "A super-resolution ultrasound method for brain vascular mapping," Medical physics, vol. 40, no. 11, p. 110701, 2013.

[21]. B. Cox and P. Beard, "Imaging techniques: Super-resolution ultrasound," Nature, vol. 527, no. 7579, pp. 451-452, 2015.

[22]. C. Errico, J. Pierre, S. Pezet, Y. Desailly, Z. Lenkei, O. Couture, and M. Tanter, "Ultrafast ultrasound localization microscopy for deep super-resolution vascular imaging," Nature, vol. 527, no. 7579, pp. 499-502, 2015.

[23]. T. Dertinger, R. Colyer, R. Vogel, J. Enderlein, and S. Weiss, "Achieving increased resolution and more pixels with superresolution optical fluctuation imaging (sofi)," Optics express, vol. 18, no. 18, pp. 18 875-18 885, 2010.

[24]. T. Taxt and R. Jirík, "Superresolution of ultrasound images using the first and second harmonic signal," Ultrasonics, Ferroelectrics, and Frequency Control, IEEE Transactions on, vol. 51, no. 2, pp. 163-175, 2004.

[25]. D. Kouame and M. Ploquin, "Super-resolution in medical imaging: An illustrative approach through ultrasound," in Biomedical Imaging: From Nano to Macro, 2009. ISBI'09. IEEE International Symposium on. IEEE, 2009, pp. 249-252.

[26]. G. Clement, J. Huttunen, and K. Hynynen, "Super-resolution ultrasound imaging using back-projected reconstruction," The Journal of the Acoustical Society of America, vol. 118, no. 6, pp. 3953-3960, 2005.

[27]. J. N. Wright, "Image formation in diagnostic ultrasound," 1997.

[28]. J. W. Goodman, "Introduction to fourier optics," 2005.

[29]. T. Szabo, Diagnostic Ultrasound Imaging: Inside Out, ser. Academic Press series in biomedical engineering. Elsevier Academic Press, 2004. [Online]. Available: https://books.google.com/books?id=-Fd1Pkeh2T0C.

[30]. B. R. Hunt, "Super-resolution of imagery: understanding the basis for recovery of spatial frequencies beyond the diffraction limit," in Information, Decision and Control, 1999. IDC 99. Proceedings. 1999. IEEE, 1999, pp. 243-248.
[31]. E. J. Candes and C. Fernandez-Granda, "Towards a mathematical theory of super-resolution," CoRR, vol. abs/1203.5871, 2012.
[32]. B. E. Treeby, J. Jaros, A. P. Rendell, and B. Cox, "Modeling nonlinear ultrasound propagation in heterogeneous media with power law absorption using a k-space pseudospectral method," The Journal of the Acoustical Society of America, vol. 131, no. 6, pp. 4324-4336, 2012.
[33]. F. S. Foster, C. J. Pavlin, K. A. Harasieqicz, D. A. Christopher and D. H. Turnbul, "Advances in Ultrasound Biomicroscopy," Ultrasound in Med. & Biol., Vol. 26, No. 1, pp. 1-27, 2000.
[34]. F. Viola, M. A. Ellis and W. F. Walker, "Time-Domain Optimized Estimator for Ultrasound Imaging: Initial Development and Results," IEEE Trans Med Imaging. 2008 January; 27(1); 99-110. Doi 10.1109/TMI. 2007.93579.
[35]. M. A. Ellis and W. F. Walker, "Super-Resolution Image Reconstruction with Reduced Computational Complexity," 2009 IEEE International Ultrasound Symposium Proceeding, pp. 2351-2354.
[36]. M. A. Ellis and W. F. Walker, "Super-Resolution Image Reconstruction with Diffuse Source Models," Ultrasound Med Biol. 2010 June; 36(6): 967-977. Doi:10.1016/j.ultrasmedbio.2010.03.002.
[37]. Y. Yankelevsky, Z. Freedman and AFeuer, "Component Based Modeling of Ultrasound Signals," arXiv: 1603.00273v1.
[38]. W. F. Walker and M. Ellis, U.S. Pat. No. 8,818,064 B2, Aug. 26, 2014.
[39]. R. Tibshirani, "Regression shrinkage and selection via the lasso," J. Roy. Stat. Soc. B, vol. 58, pp. 267-288, 1996.

The invention claimed is:

1. An ultrasound imaging system comprising:
an ultrasound transducer configured to send ultrasound into an object comprising an array of known scatterers from plural transducer elements operating as transmitting elements and to receiving echoes from the object at fewer but no less than two separate transducer elements operating as receiving elements, wherein the transmitting and receiving is free of apodization and beam forming;
a computer processor configured to generate a sensing matrix comprising the echoes that said fewer receiving elements of the transducer received from the array of known scatterers, wherein the processor is configured to send the sensing matrix comprising the echoes to computer memory for storage;
the computer processor being further configured to estimate reflectance coefficients of locations in the object that spatially relate to said array of known scatterers by applying a constrained least squares estimate to fit the echoes received from the object comprising the array of known scatterers to a combination of the sensing matrix and reflectance coefficients of said location in the object while minimizing L2-norm fitting error of the constrained least squares estimate;
and said computer processor is further configured to produce and display an ultrasound image of the object comprising the array of known scatterers as a function of said estimated reflectance coefficients.

2. The system of claim 1, in which said transmitting elements of the transducer are physically separate and spaced from said receiving elements.

3. The system of claim 1, in which the constrained least squares estimate that the computer processor applies is a bounded least squares estimate in which reflectance coefficients of locations in the object are estimated while constrained to a selected range of values.

4. The system of claim 3, in which said range of values is from zero to one.

5. The system of claim 1, in which said computer processor is configured to include in said least squares estimate a cost function that includes L1-norm of the reflectance coefficients of said locations in the object.

6. The system of claim 5, in which said computer processor is configured to include in said least squares estimate a cost function that includes a linear combination of the L1-norm and the L2-norm of the reflectance coefficients of said locations in the object.

7. An ultrasound imaging system comprising:
an ultrasound transducer configured to send ultrasound into an object comprising an array of known scatterers from plural transducer elements acting as transmitting elements and to receiving echoes from the object at fewer but no less than two separate transducer elements acting as receiving elements, wherein the transmitting and receiving is free of apodization and beam forming;
a computer processor configured to generate a sensing matrix comprising the echoes that said fewer receiving elements of the transducer received from the array of known scatterers, wherein the processor is configured to send the sensing matrix comprising the echoes to computer memory for storage;
the computer processor being further configured to estimate reflectance coefficients of locations in the object that spatially relate to said array of known scatterers by applying a weighted least squares estimate to fit the echoes received from the object to a combination of the sensing matrix and reflectance coefficients of said location in the object;
and said computer processor is further configured to produce and display an ultrasound image of the object comprising the array of known scatterers as a function of said estimated reflectance coefficients.

8. The system of claim 7, in which said transmitting elements of the transducer are physically separate and spaced from said receiving elements.

9. The system of claim 7, in which the least squares estimate that the computer processor applies is a bounded least squares estimate in which values of the reflectance coefficients of locations in the object are estimated while constrained to a selected range of values.

10. The system of claim 9, in which said range of values is from zero to one.

11. The system of claim 7, in which said computer processor is configured to include in said least squares estimate a cost function that includes L1-norm of the reflectance coefficients of said locations in the object.

12. The system of claim 7, in which said computer processor is configured to include in said least squares estimate a cost function that includes a linear combination of L1-norm and L2-norm of the reflectance coefficients of said locations in the object.

13. An ultrasound imaging system comprising:
an ultrasound transducer having transducer elements configured to detect both amplitude and phase of echoes of ultrasound energy sent into an object comprising an array of known scatterers by said transducer, wherein the transmitting and receiving is free of apodization and beam forming;

a computer processor configured to generate echoes from an array of known scatterers, wherein the processor is configured to send the sensing matrix comprising the echoes to computer memory for storage;

the computer processor being further configured to estimate reflectance coefficients of locations in the object that spatially relate to said array of known scatterers by applying a bounded least squares estimate to fit the echoes received from the object to a combination of the sensing matrix and reflectance coefficients of said locations in the object;

wherein said estimate is configured to constrain the reflectance coefficients of said locations in the object to positive values between a minimum and a maximum; and said computer processor is further configured to produce and display an ultrasound image of the object comprising the array of known scatterers as a function of said estimated reflectance coefficients.

14. The system of claim 13, in which the constrained values range from zero to one.

15. The system of claim 13, in which the cost function in the least squares estimate includes L1-norm of the reflectance coefficients of said location in the object.

16. The system of claim 13, in which said computer processor is configured to include in said least squares estimate a cost function that includes a linear combination of L1-norm and L2-norm of the reflectance coefficients of said locations in the object.

17. An ultrasound imaging method comprising:

sending ultrasound into an object from plural transducer elements and receiving echoes from the object comprising an array of known scatterers at fewer but no less than two separate transducer elements, wherein the transmitting and receiving is free of apodization and beam forming;

generating a sensing matrix comprising the echoes that said fewer receiving elements of the transducer receive from array of known scatterers, sending the sensing matrix comprising the echoes to computer memory for storage;

carrying out a bounded least squares estimate with a computer to fit the echoes received from the object comprising the array of known scatterers to a combination of the sensing matrix and reflectance coefficients of said in the object spatially related to said scatterers;

wherein said estimate is configured to constrain the reflectance coefficients of said locations in the object to positive values between zero and one;

and producing and displaying an ultrasound image of the object comprising the array of known scatterers as a computer-calculated function of said estimated reflectance coefficients.

18. The method of claim 17, in which estimate utilizes a cost function that includes L1-norm of the reflectance coefficients of said locations in the object.

19. The method of claim 17, in which said estimate utilizes a cost function that includes a linear combination of L1-norm and L2-norm of the reflectance coefficients of said locations in the object.

20. An ultrasound imaging process comprising:

detecting, at two or more separate receiving elements of an ultrasound transducer, both amplitude and phase of echoes generated by ultrasound energy sent into an object comprising an array of known scatterers, wherein the transmitting and receiving is free of apodization and beam forming;

generating a sensing matrix comprising the echoes that said receiving elements of the transducer receive from the array of known scatterers, sending the sensing matrix comprising the echoes to computer memory for storage;

carrying out an least squares estimate with a computer programmed to fit the echoes received from the object comprising the array of known scatterers to a combination of the sensing matrix and reflectance coefficients of location in the object spatially related to said scatterers through a bounded least squares estimate;

wherein said estimate is configured to constrain the amplitude properties of said locations in the object to positive values between a minimum and a maximum and the phase properties of said locations in the object to another range of values; and producing and displaying an ultrasound image of the object comprising the array of known scatterers as a computer-calculated function of said estimated reflectance coefficients.

21. The process of claim 20, in which the positive values to which said amplitude properties are constrained range from zero to one.

22. The process of claim 20, in which said estimate utilizes a cost function that includes L1-norm of the reflectance coefficients of said locations in the object.

23. The process of claim 20, in which said estimate utilized a cost function that includes a linear combination of L1-norm and L2-norm of the reflectance coefficients of said locations in the object.

24. An ultrasound imaging system comprising:

an ultrasound transducer configured to send ultrasound into an object comprising an array of known scatterers from one or more transducer elements operating as transmitting elements and to receive echoes from the object at no less than two separate transducer elements operating as receiving elements, wherein the transmitting and receiving is free of apodization and beam forming;

a computer processor configured to generate a sensing matrix comprising the echoes that said no less than two receiving elements of the transducer received from the array of known scatterers, wherein the processor is configured to send the sensing matrix comprising the echoes to computer memory for storage;

the computer processor being further configured to estimate reflectance coefficients of locations in the object that spatially relate to said array of known scatterers by applying a constrained least squares estimate to fit the echoes received from the object comprising the array of known scatterers to a combination of the sensing matrix and properties of said location in the object while minimizing L2-norm fitting error of the constrained least squares estimate;

and said computer processor is further configured to produce and display an ultrasound image of the object comprising the array of known scatterers as a function of said estimated reflectance coefficients.

25. The system of claim 24, wherein said receiving elements and said transmitting elements are collocated in said transducer.

26. The system of claim 24, in which said receiving elements are physically separated and electrically isolated from said transmitting elements.

27. The system of claim 24, in which said transmitting elements are a single physical transmitting element.

\* \* \* \* \*